(12) United States Patent
Yip et al.

(10) Patent No.: US 10,022,542 B2
(45) Date of Patent: Jul. 17, 2018

(54) LOW POWER COCHLEAR IMPLANTS

(71) Applicants: Massachusetts Eye & Ear Infirmary, Boston, MA (US); Massachusetts Institute of Technology, Cambridge, MA (US)

(72) Inventors: Marcus Yip, Cambridge, MA (US); Anantha Chandrakasan, Belmont, MA (US); Konstantina Stankovic, Boston, MA (US)

(73) Assignees: Massachusetts Eye & Ear Infirmary, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/037,782

(22) PCT Filed: Nov. 25, 2014

(86) PCT No.: PCT/US2014/067405
§ 371 (c)(1),
(2) Date: May 19, 2016

(87) PCT Pub. No.: WO2015/077773
PCT Pub. Date: May 28, 2015

(65) Prior Publication Data
US 2016/0287870 A1 Oct. 6, 2016

Related U.S. Application Data

(60) Provisional application No. 62/012,896, filed on Jun. 16, 2014, provisional application No. 61/908,237, filed on Nov. 25, 2013.

(51) Int. Cl.
*A61N 1/36* (2006.01)
*A61N 1/378* (2006.01)
(Continued)

(52) U.S. Cl.
CPC ......... *A61N 1/36032* (2013.01); *A61N 1/025* (2013.01); *A61N 1/378* (2013.01);
(Continued)

(58) Field of Classification Search
None
See application file for complete search history.

(56) References Cited

U.S. PATENT DOCUMENTS 6,954,163 B2 * 10/2005 Toumazou ................ G06J 1/00
341/110
7,346,397 B2 3/2008 Money et al.
(Continued)

FOREIGN PATENT DOCUMENTS

CN 101614566 8/2011

OTHER PUBLICATIONS

D. J. Young, et al, MEMS Capacitive Accelerometer-Based Middle Ear Microphone, IEEE Trans. on Bio. Eng., vol. 59, p. 3283 (2012).
(Continued)

*Primary Examiner* — Brian T Gedeon
(74) *Attorney, Agent, or Firm* — Fish & Richardson P.C.

(57) ABSTRACT

In one aspect, the disclosure features systems for providing auditory signals to a subject. The systems include a sensor front-end circuit configured to be connected to an acoustic sensor and to convert analog signals received from the acoustic sensor to digital electric signals. The systems further include a sound processor circuit configured to be connected to the sensor front-end circuit and receive the electric signals provided by the sensor front end circuit. The sound processor includes multiple filters that spectrally decompose the received electrical signals into multiple spectral channels during operation of the system. The multiple spectral channels include at least a low frequency channel and a high frequency channel and the sound pro-
(Continued)

cessor circuit is configured to operate the low frequency channel at a sample rate lower than a sample rate of the high frequency channel.

15 Claims, 22 Drawing Sheets

(51) Int. Cl.
    *A61N 1/02* (2006.01)
    *A61B 5/00* (2006.01)
    *A61B 5/11* (2006.01)

(52) U.S. Cl.
    CPC ........... *A61B 5/1114* (2013.01); *A61B 5/6878* (2013.01); *A61B 2560/0219* (2013.01); *A61B 2562/0204* (2013.01)

(56) References Cited

U.S. PATENT DOCUMENTS

| | | |
|---|---|---|
| 8,539,012 B2 | 9/2013 | Clark |
| 9,014,813 B2 * | 4/2015 | Foutz ................. A61N 1/36125 607/12 |
| 2011/0106211 A1 | 5/2011 | Litvak |

OTHER PUBLICATIONS

H. A. Jenkins, et al, U.S. Phase I Preliminary Results of Use of the Otologics MET Fully-Implantable Ossicular Stimulator, Otol.-Head and Neck Surgery, 137, 206-212 (2007).

* cited by examiner

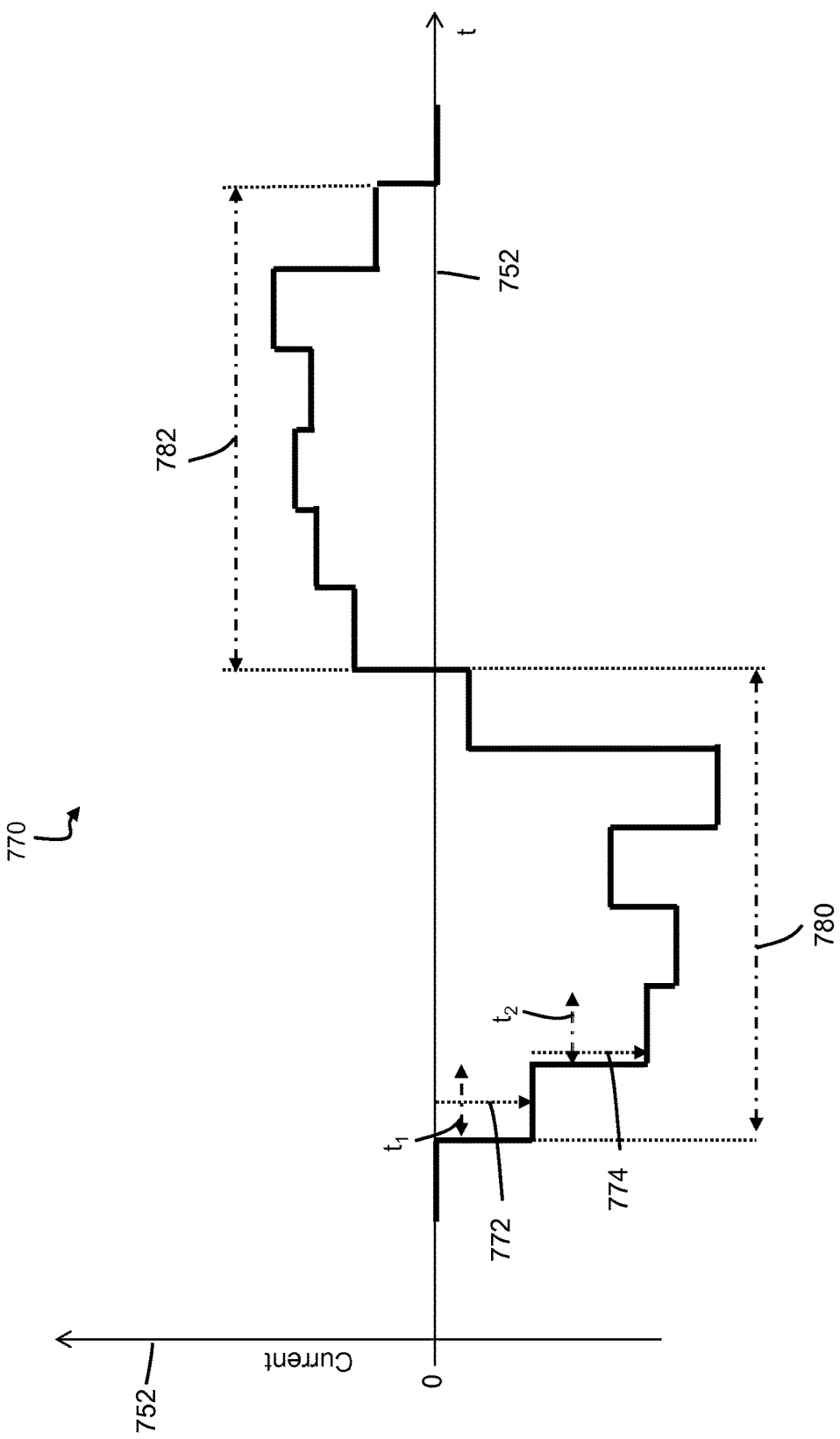

Electrode model ($Z_{Ei}$)

Tissue impedance model ($Z_{TISSUE}$)

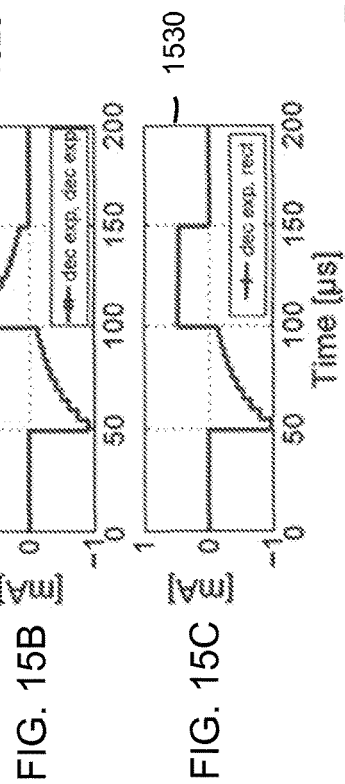
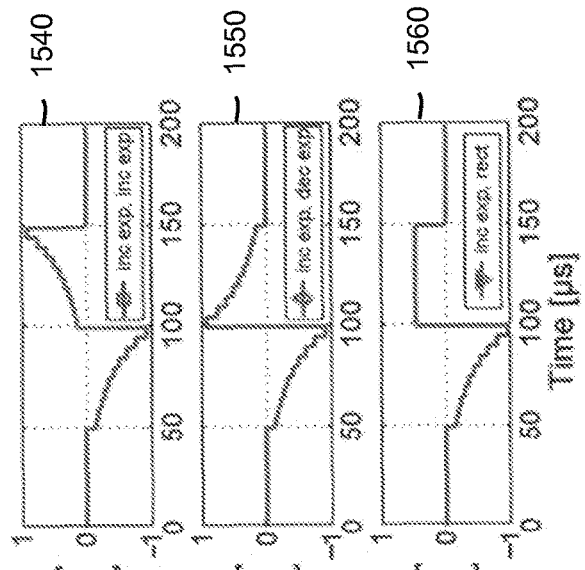
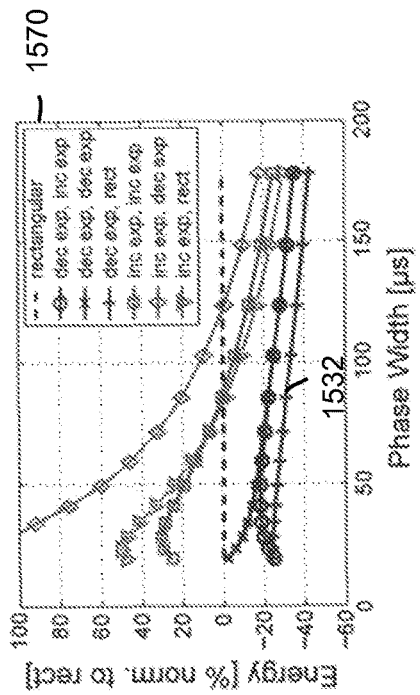
FIG. 15A
FIG. 15B
FIG. 15C
FIG. 15D
FIG. 15E
FIG. 15F
FIG. 15G

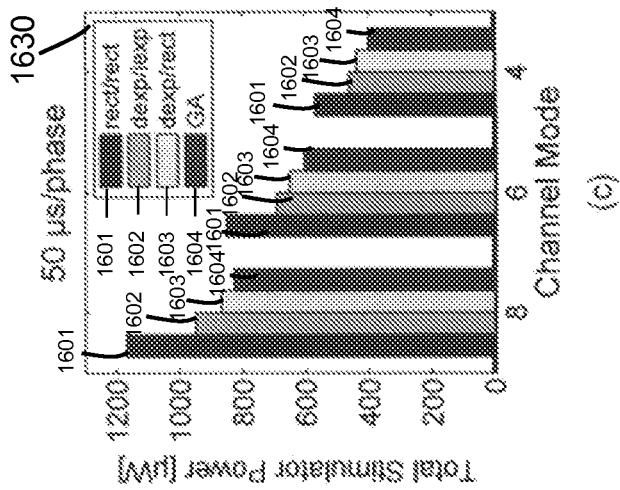
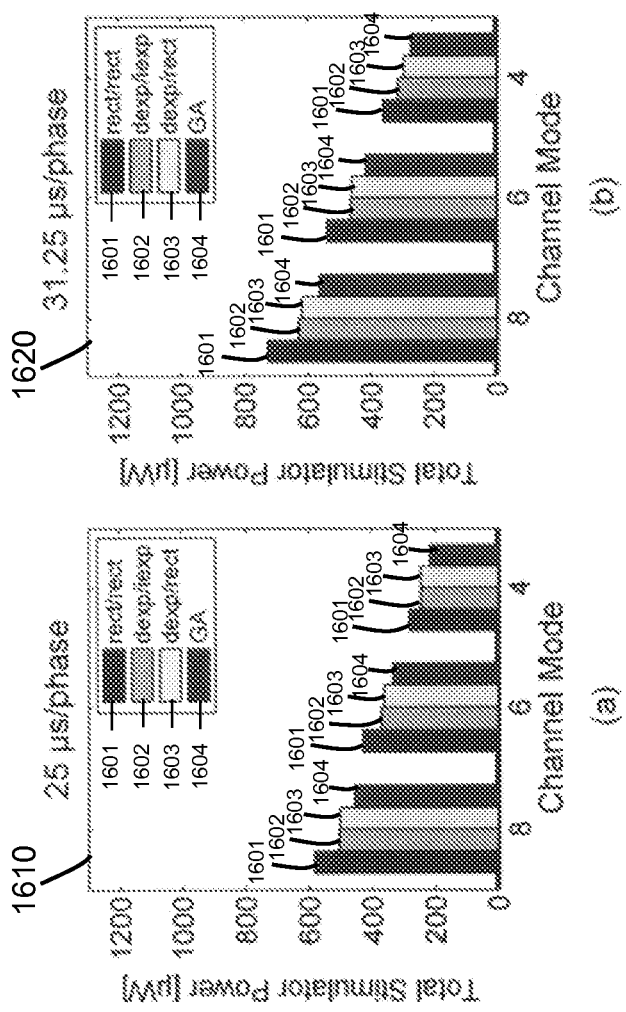

LOW POWER COCHLEAR IMPLANTS

CROSS REFERENCE TO RELATED APPLICATIONS

This application is a 371 U.S. National Application of PCT/US2014/067405, filed on Nov. 25, 2014, which claims priority from U.S. Provisional Application No. 61/908,237 filed on Nov. 25, 2013 and from U.S. Provisional Application No. 62/012,896 filed on Jun. 16, 2014, the entire contents of both of which are incorporated herein by reference.

TECHNICAL FIELD

This invention relates to cochlear implants.

BACKGROUND

Humans and other animals can suffer from conductive hearing loss, where there is damage to the ossicular chain (bones of the middle ear). Treatment options include medical or surgical treatment, or various types of hearing aids and prosthetics. Another form of hearing loss is sensorineural hearing loss, where there is damage to hair cells in the cochlea (inner ear). In this case, damage to the hair cells in the cochlea degrades the transduction of acoustic information to electrical impulses in the auditory nerve. Treatment options include hearing aids such as cochlear implants that are devices used to stimulate the auditory nerves.

Conventional cochlear implants typically include a microphone to pick up sound. The microphone is fixed external to the ear, which can raise social stigma and limit the usage of the microphone in the shower or during water sports.

SUMMARY OF THE INVENTION

This disclosure describes techniques and systems to aid hearing of subjects (e.g., human or animal subjects) using fully implantable systems that include special circuits (e.g., sensor front-end circuit, sound processor circuit, and waveform stimulator) that enable the systems to run with extremely low power requirements. In particular, the circuits can be manufactured on a single chip that is used to deliver electrical stimulation to nerve tissues in auditory systems of the subject. Circuits can operate at low power to extend usage time of the chip before its power source (e.g., battery) needs to be recharged. The chips can provide waveforms (e.g., arbitrary waveforms) used to generate energy-efficient stimulation pulses. Moreover, the small size of the chips allows them to be used in fully implantable cochlear implants for stimulating auditory nerves. The cochlear implants can include an acoustic sensor (e.g., a microphone, an accelerometer, or a piezoelectric sensor) mounted in the middle ear (e.g., contacting one of the ossicles, e.g., the malleus, e.g., at the umbo, the incus, and the stapes, or contacting the oval window of the cochlea) to efficiently detect incoming sound pressure in the ear canal. Sound detected by the acoustic sensor is processed by various circuits of the cochlear implants in a power-efficient manner. The cochlear implants provide stimulation signals to auditory nerves to aid hearing by the subject.

The techniques and systems disclosed herein enable extremely low power operation of cochlear implants by utilizing power saving techniques in various parts of the system. For example, certain circuits (e.g., sound processor circuit) can operate at less than 1.0 volt (e.g., at 0.6 V) to operate close to its minimum energy point of energy dissipation. As another example, the cochlear implants can include a waveform stimulator that operates at milli-Watt power consumption level while delivering energy above the threshold for action potential (spike) initiation in a nerve fiber. These results can be achieved by minimizing energy of the stimulus by applying electrical pulses with a highly energy-efficient waveform shape to the nerve fiber.

In one aspect, the disclosure features systems for providing auditory signals to a subject. The systems include a sensor front-end circuit configured to be connected to an acoustic sensor and to convert analog signals received from the acoustic sensor to digital electric signals. The systems further include a sound processor circuit configured to be connected to the sensor front-end circuit and receive the electric signals provided by the sensor front end circuit. The sound processor includes multiple filters that spectrally decompose the received electrical signals into multiple spectral channels during operation of the system. The multiple spectral channels include at least a low frequency channel and a high frequency channel and the sound processor circuit is configured to operate the low frequency channel at a sample rate lower than a sample rate of the high frequency channel.

In some implementations, during operation of the system, the system can be configured to send a clock signal and a control signal into a gate, and use the output of the gate to clock-gate filters of the spectral channels that are not used to provide the auditory signals.

In some implementations, the sensor front-end circuit can include a charge amplifier circuit, a programmable gain circuit, and an analog-to-digital converter (ADC) circuit.

In some implementations, the sound processor circuit can include a reconfigurable filter bank that include the multiple filters, and the reconfigurable filter bank can be configured to change the number of spectral channels used to provide auditory signals. The sound processor circuit can be reconfigurable to operate in 4-channel, 6-channel, or 8-channel modes. Power consumption of the sound processor circuit can be linear to the number of operating spectral channels within 15% or less. The reconfigurable filter bank can be configured to adjust the bandwidth and center frequency of at least one of the filters. The multiple filters can be configured to receive coefficients signals input that are quantized to 8-bit precision.

Additional implementations can include a waveform stimulator that includes a digital waveform interface circuit, an electrode switch matrix, and a current source. The waveform stimulator can be configured to provide a waveform shape that is more energy-efficient than a rectangular waveform with the same pulse width. The waveform stimulator can be configured to provide a plurality of waveform shapes. The systems can include a calibration circuit configured to measure hearing thresholds for the plurality of waveform shapes and select a waveform shape having a low energy. The waveform stimulator can be configured to provide a waveform and to adjust the shape of the waveform. The waveform stimulator can include only one current source. During operation, the systems can consume 600 μW or less during normal conversation.

In another aspect, the disclosure features implantable systems for providing auditory signals to a subject. The systems include a sound processor circuit that includes multiple filters that spectrally decompose received electrical signals into multiple spectral channels during operation of the system. The systems further include a waveform stimulator including a digital waveform interface circuit and an electrode switch matrix. The waveform stimulator is configured to receive output signals from the multiple spectral channels and to generate an auditory signal.

In some implementations, the waveform stimulator can include a two-stage level shifter that connects the digital wave form interface circuit and the electrode switch matrix. The waveform stimulator can include a single current source.

In some implementations, the waveform stimulator can include a fast-settling current source. The waveform stimulator can be configured to generate a waveform shape which has an energy of 28% or less than that of a rectangular waveform with the same total pulse width.

In another aspect, the disclosure features methods for providing auditory signals to a subject. The methods include determining a waveform using a heuristic algorithm where the waveform shape includes a cathodic phase and an anodic phase, and each of the cathodic phase and anodic phase differs in shape from a cathodic phase and an anodic phase in a rectangular waveform.

In some practices, the methods can include generating an electrical current pulse based on the determined waveform, and applying the generated current pulse to stimulate auditory nerves of the subject. The cathodic phase can exponentially decrease over time.

In some implementations, the waveform shape can be determined based on a parameter selected from a group consisting of a phase width, duty cycle, and number of steps/width of the heuristic algorithm. The determined waveform can have an energy of 28% or less than that of a rectangular waveform with a same total pulse width.

In some practices, the methods can include providing a plurality of current pulses with different waveform shapes to the subject using the waveform stimulator, and measuring hearing thresholds for the different waveform shapes. The methods can include selecting a waveform shape with a lower energy for the measured threshold than another waveform shape.

In some implementations, the method steps described in the preceding paragraphs are implemented before implanting the waveform stimulator to the subject.

In some implementations, the method steps described in the preceding paragraphs are implemented after implanting the waveform stimulator to the subject.

Additional implementations can include detecting vibration signals using an acoustic sensor, and generating electric signals by processing the detected vibration signals using a sensor front-end circuit. The methods can include spectrally decomposing the electric signals using a sound processor circuit to generate decomposed information, and using the decomposed information to apply the generated current pulse to multiple spectral channels for stimulating auditory nerves of the subject. Multiple spectral channels can receive differently scaled amplitudes of the wave form. The methods can include reconfiguring the number of spectral channels used to stimulate the auditory nerves.

The techniques and systems disclosed in this specification provide numerous benefits and advantages (some of which can be achieved only in some of the various aspects and implementations) including the following. Given the new systems, the cochlear implants can be implemented on a single chip that is fully implantable (including the acoustic sensor) inside the ear of a subject. This can be aesthetically pleasing and convenient for the subject, because the cochlear implants can be fully implantable and will not be seen external to the ear. In addition, a subject can use the cochlear implant in the shower or during water sports without damage to the implant.

In general, the disclosed techniques can be used to significantly reduce the power consumption of a cochlear implant in a variety of ways. For example, the cochlear implants can operate at overall power consumption of 600 µW or less while stimulating auditory nerves at their threshold of action potential. A waveform stimulator of the implant can generate arbitrary waveforms that have shapes that minimize the energy needed to stimulate auditory nerves. In some cases, various parameters (e.g., shape, pulse duration, and duty cycle) of the waveform can be fine-tuned for a specific subject or environment in real-time.

Because the energy needed to stimulate the nerves takes up a significant portion of the power consumption of the cochlear implant, power reduction of the waveform stimulator can enhance the operation time of the implant for a given capacity of battery. As another example, the cochlear implant can include a sound processor circuit that utilizes a multi-rate reconfigurable filter bank. The filter bank can operate different spectral channels at different sample frequencies that reduce power consumption of the sound processor circuit. Moreover, the reconfigurability of the filter back allows selection of the optimum number of spectral channels for different subjects so that unnecessary channels can be turned off. In some cases, when available battery level is low, the cochlear implant can be switched to an operation mode using a lower number of channels to save battery power until the battery is recharged. These approaches lead to power savings of the cochlear implant.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

BRIEF DESCRIPTION OF THE DRAWINGS

FIG. 7C is a schematic of an example a waveform of an electrical pulse.

FIGS. 15A-G are representations of various waveforms generated by an electronic processor and their energies.

FIGS. 16A-C are a series of plots of measured power consumption for generating pulses of various waveforms.

DETAILED DESCRIPTION

The methods and systems described herein can be implemented in many ways. Some useful implementations are described below. The scope of the present disclosure is not limited to the detailed implementations described in this section, but is described in broader terms in the claims.

Anatomy of the Ear

Figure 1:
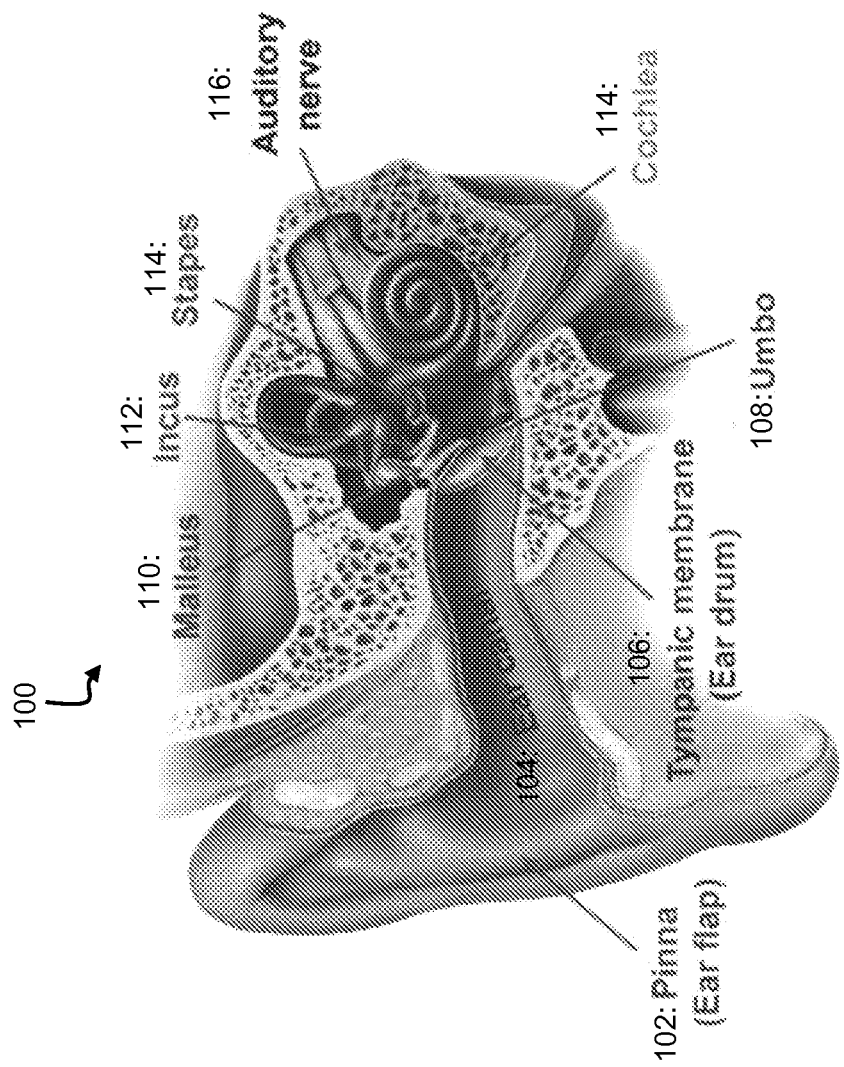
FIG. 1 is a schematic of a cross section of a human ear.

The ears of subjects, e.g., humans and animals such as mammals, have a similar anatomy. The human ear is an auditory system that transforms acoustical energy to electrical energy that is applied to the auditory nerve. FIG. 1 is a schematic of a cross section of a human ear 100, which is separated into the outer ear, middle, and inner ear.

The outer ear includes the pinna 102, ear canal 104, and tympanic membrane 106 (ear drum). Umbo 108 is the most depressed part of the tympanic membrane when viewed from within the ear canal. Sound pressure waves enter the pinna 102 and vibrate the tympanic membrane 106, which motion couples to the ossicular chain that includes three small bones called the malleus 110, incus 112, and stapes 114 of the middle ear. The motion of the stapes 114 on the oval window of the cochlea moves fluid inside the cochlea of the inner ear. Motion of the hair cells of the cochlea due to the motion of the cochlear fluid generates electric pulses to the auditory nerve, which the brain interprets as sound. The length of the hair cells is shortest near the oval window (base) of the cochlea and increases toward the round window at the end (apex) of the cochlea. Higher frequency waves excite the hair cells near the base and lower frequency waves excite hair cells at the apical end of the cochlea as the resonant frequency of each hair cell depends on its length.

Conductive hearing loss occurs when there is damage to the ossicular chain, while sensorineural hearing loss occurs when there is damage to the hair cells in the cochlea. In the latter case, a cochlear implant can be used to generate electric pulses that are applied to the auditory nerve to help restore hearing. This specification relates to cochlear implants to aid hearing.

Devices

Figure 2:
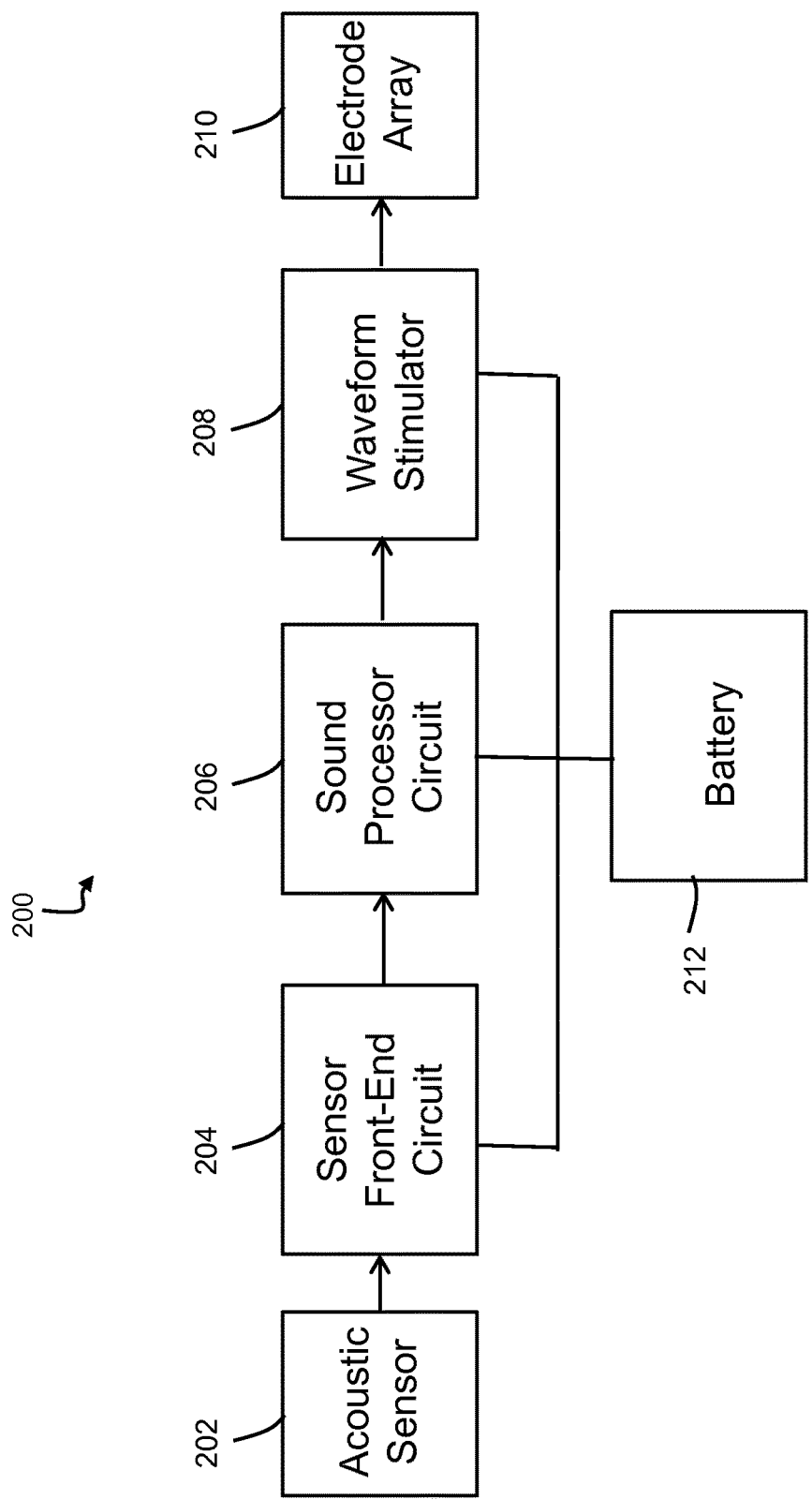
FIG. 2 is a schematic block diagram of components in a low power cochlear implant as described herein.

FIG. 2 is a schematic of a cochlear implant 200 including components 202-212. Acoustic sensor 202 (e.g., a microphone, an accelerometer, or a piezoelectric sensor) can be mounted to contact one of the ossicles, e.g., on the malleus, such as on the umbo of the malleus. As used herein, an acoustic sensor is any device that can convert sound or vibration into an electrical signal, e.g., an analog or digital electrical signal. The acoustic sensor 202 detects the motion of the umbo and generates electrical signals, which are received by sensor front-end circuit 204. The sensor front-end circuit 204 can amplify the received electrical signals and can convert analog signals into digital signals. As a result, the sensor front-end circuit 204 can send digital electrical signals to sound processor circuit 206. In some implementations, acoustic sensor 202 can provide a digital electrical signal. In this case, the sensor front-end circuit 204 may not need to amplify and convert the analog signals received from the acoustic sensor 202 into digital signals.

The sound processor circuit 206 spectrally decomposes the received signals into multiple channels. Different channels represent different spectral ranges of sound perceived by a subject. The outputs of the channels are sent to waveform stimulator 208 to control electric pulses delivered by electrode array 210. The waveform stimulator 208 generates waveforms that are applied to the electrode array 210 as electric pulses through an electrode switch matrix. In this way, the electric pulses can stimulate the auditory nerve of the subject according to the detected sound and processed electrical signals. Battery 212 can provide power to various components (e.g., sensor front-end circuit 204, sound processor circuit 206, waveform stimulator 208) of cochlear implant 200. Detailed implementations of various components are described in the following sections.

Figure 3:
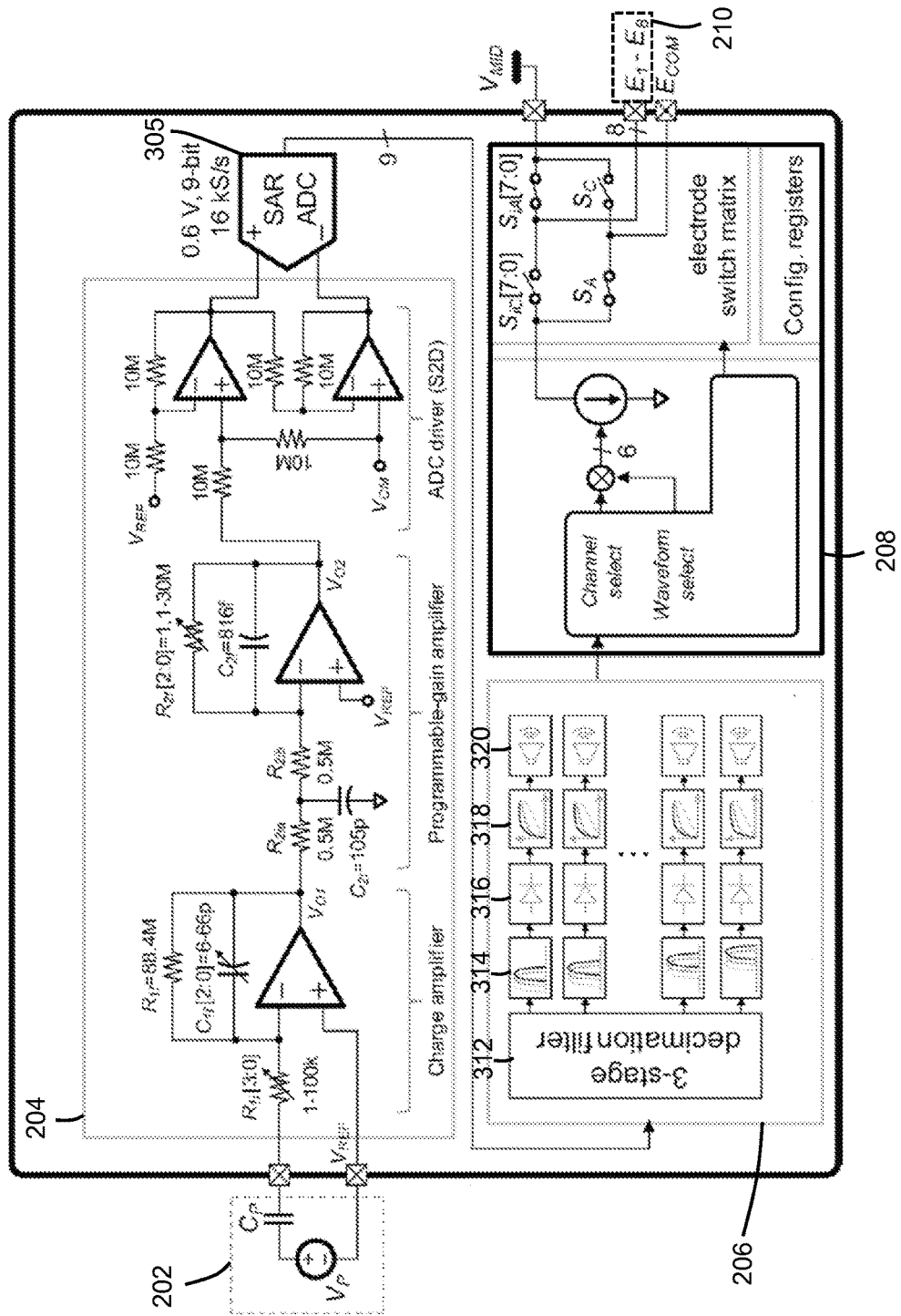
FIG. 3 is a schematic of an example of a circuit diagram of one embodiment of a low power cochlear implant.

FIG. 3 is a schematic of one example of cochlear implant 200. In this example, digital-to-analog converter (ADC) 305 (e.g., successive approximation or "SAR" ADC) receives signals from sensor front-end circuit 204 and sends the converted signal to sound processor circuit 206. In some implementations, the sensor-front end circuit 204 includes the ADC 305.

The sound processor circuit 206 can include a variety of steps for processing the received signals. For example, the received signals pass through a filter (e.g., a 3-stage decimation filter 312 to down-sample an input clock signal into lower sample rates) and are spectrally decomposed by filter bank 314 so as to form multiple channels. Following the filter bank 314, the envelope of each channel is extracted by envelope extractor 316. For example, the extractor 316 can extract the envelope by passing respective signals through a rectifying diode and a low-pass filter. Then signals of each channel can be compressed by compressor 318. This is to take account of the loudness growth function of electrical hearing that describes the linear relationship between acoustic sound intensity in decibel (dB) sound pressure level (SPL) and electric stimulation intensity in amperes. Optionally, the dynamic range of signals in each channel can adjusted by fitting circuit 320 to match individual threshold (THR) and most-comfortable-level (MCL) specific to a subject.

Detailed description of various components of cochlear implant 200 is described in the following sections.

Acoustic Sensor

An acoustic sensor 202 is small enough to be implanted in the middle ear and to replace conventional microphones installed external to the ear. The acoustic sensor 202 is small and light weight so that the presence of the acoustic sensor 202 does not dampen the natural frequency response of the middle ear. In other words, the mass-loading by the sensor is designed to be negligible if the sensor is implanted to contact one of the bones in the ossicular chain so as to avoid performance reduction of the ossicular chain. Moreover, the acoustic sensor 202 can be mechanical impedance matched to effectively pick up sound waves by vibration of the bones, e.g., the umbo of the malleus. The acoustic sensor 202 can also be implanted beneath skin portions away from the ear, in a location to avoid unwanted pickup of vibrations due to talking or chewing.

The acoustic sensor 202 has the sensitivity and dynamic range needed for hearing. This is taken into consideration in the design of the acoustic sensor 202 and sensor front-end circuit 204. Moreover, the electrical impedance between the acoustic sensor 202 and the sensor front-end circuit 204 can be matched so the sensor front-end circuit 204 can efficiently receive electrical currents from the acoustic sensor 202, thereby increasing the sensitivity. In some implementations, the acoustic sensor 202 can detect sounds from 300 Hz to 10 kHz over a 50 dB dynamic range from 40 to 90 dB SPL. In some implementations, a pre-emphasis of +6 dB/octave can be embedded in the output of acoustic sensor 202. Generally, the acoustic sensor 202 can detect frequencies from 10 Hz to 60 kHz or more (e.g., 80 kHz or more, 120 kHz or more, 160 kHz or more), and electrical signals with such frequencies can be processed by a cochlear implant to generate stimulus pulses corresponding to these frequencies.

Acoustic sensor 202 can be designed to have a noise floor level to provide sufficient sensitivity and a mass that does not significantly deter the function of the umbo. To determine the noise floor level and mass, laser Doppler vibrometery (LDV) can be used to measure the vibration velocity of the location to which the acoustic sensor will be mounted, e.g., on the umbo. For example, for pure tones from 0.1 to 19 kHz sound input, the integrated noise is about 10 $\mu m_{rms}$ (1 g=9.8 m/s$^2$) over 8 kHz bandwidth and a minimum detectable sound of 40 dB SPL leads to a noise floor of about 0.1 $\mu g_{rms}$/sqrt(Hz). The noise of acoustic sensor 202 can be lower than this noise floor of 0.1 $\mu g_{rms}$/sqrt(Hz). The vibration velocity of the umbo can be measured by varying the mass of metal, e.g., copper disks attached to the umbo. By determining the mass that negligibly affects the umbo vibration, the mass-limit of the acoustic sensor 202 can be identified, for example, to be less than 20 mg.

In some implementations, acoustic sensor 202 can be an accelerometer that detects motion of a middle ear bone, e.g., the malleus, for example, the umbo of the malleus. The accelerometer can be small enough to be implanted in the middle ear, and directly or indirectly (through a lever) contact the ossicle. For example, accelerometers can include piezoelectric, piezoresistive, or capacitive components that convert mechanical motion to an electrical signal. In some implementations, the accelerometer can detect tilt and/or vibration. Accelerometers can include SQ-SEN® models, SQ-MIN® models, ADXL362®, or LIS3DH®. Accelerometers can include micro electro-mechanical (MEMS) devices having a cantilever beam. Examples of accelerometers are described in D. J. Young, et al, MEMS Capacitive Accelerometer-Based Middle Ear Microphone, IEEE Trans. on Bio. Eng., vol. 59, p. 3283 (2012) and U.S. patent application Ser. No. 13/529,011 to T. M. Beckerle, filed on Jun. 21, 2012 and published on Jan. 17, 2013.

In some other implementations, acoustic sensor 202 can be a microphone that directly converts vibrating sound pressure in air to an electrical signal. The microphone can be implanted beneath the skin close to the ear. The microphone can be wired to circuits that process the electrical signal provided from the microphone. Examples of microphones are described in H. A. Jenkins, et al, U.S. Phase I Preliminary Results of Use of the Otologics MET Fully-Implantable Ossicular Stimulator, Otol.-Head and Neck Surgery, 137, 206 (2007) and U.S. Pat. No. 7,346,397 to D. Money, filed on Jun. 29, 2001.

In some implementations, acoustic sensor 202 can be a piezoelectric sensor. For example, the acoustic sensor 202 can be made from Lead-Zirconate-Titanate (PZT). The acoustic sensor 202 can be made from two or more layers of piezoelectric materials. In some implementations, the acoustic sensor 202 can be made from a single layer of piezoelectric material.

Figure 4A:
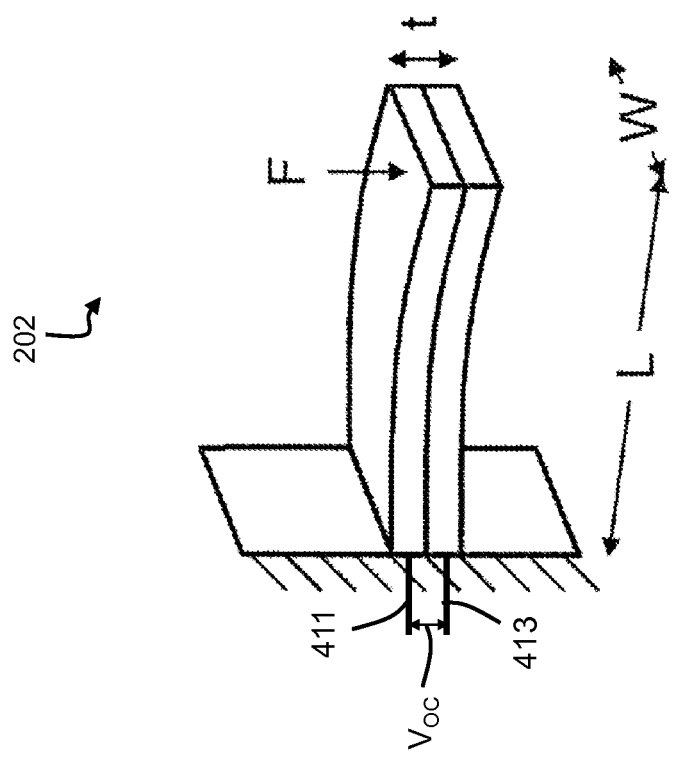
FIG. 4A is a schematic of an example of an acoustic sensor in the form of a piezoelectric cantilever design.

FIG. 4A is a schematic of an example of the acoustic sensor 202 made from piezoelectric material, which is clamped on one end like a cantilever. The other end can be placed in contact with a middle ear ossicle, such as the incus, stapes, or malleus, e.g., with the umbo of the malleus. When the umbo vibrates, the umbo exerts a force F on the sensor as illustrated in FIG. 4A. As the force F bends the acoustic sensor 202, an open circuit voltage $V_{OC}$ is generated across two terminals 411 and 413 of the acoustic sensor 202 according to equation 1 (Eq. (1)):

$$V_{OC} = g_{31}\left(\frac{3L}{2Wt}\right)F = g_{31}\left(\frac{3L}{2Wt}\right)mA_U(f)P_{EC} \quad (1)$$

where W, L, and t are dimensions of sensor depicted in FIG. 4A. $g_{31}$ is the piezoelectric transverse voltage coefficient, which for example, can be about $-11.6\times10^{-3}$ V·m/N for typical piezoelectric materials. Force F applied by the umbo can be calculated from the ear canal pressure $P_{EC}$ according to the relation $F=mA_U(f)P_{EC}$, where m is the mass of acoustic sensor 202 and $A_U(f)$ is the umbo acceleration normalize by $P_{EC}$. Typically, $A_U(f)$ is about 1 to 2 m/s$^2$/Pa.

In the example illustrated in FIG. 4A, the acoustic sensor 202 has W=3 mm, L=3 mm, and t=0.5 mm. Using density 7800 kg/m$^3$ of the PZT, mass m of the acoustic sensor 202 can be calculated to provide $V_{OC}$ ranging from 0.7 $\mu V_{rms}$ to 2.4 $\mu V_{rms}$ for sound pressure levels from 40 to 90 dB SPL. Such range of $V_{OC}$ is sufficiently larger than noise so as to be detected by sensor front-end circuit 204. Generally, the acoustic sensor 202 can be cut in other dimensions and shapes with selected mass than described in relation to FIG. 4A. In some implementations, wires connected to the acoustic sensor 202 can be shielded and/or the sensor front-end circuit 204 can be placed close to the sensor with a wire connection length of 10 mm or less (e.g., 15 mm or less, 20 mm or less), thereby reducing any electromagnetic interference affecting the acoustic sensor 202.

In some implementations, acoustic sensor 202 can be fixed (e.g., using a tissue-safe adhesive) on a rigid rod (e.g., a needle-like rod). When the acoustic sensor 202 includes a piezoelectric sensor, a support can be used to fix one end of the piezoelectric sensor to a bony wall within the middle ear, while the other end of the piezoelectric sensor is fixed to the rod. The rod can directly contact the ossicle, and the vibration of the ossicle is transferred through the rod to the acoustic sensor 202. In this case, the acoustic sensor 202 is not directly in contact with the ossicle. The rod can be a thin bar made from metal, plastic, or ceramic that is sufficiently rigid to effectively transfer vibrations of the ossicle to the sensor.

Acoustic sensor 202 can have numerous advantages such as having a small size, mass, customizability (by being cut in any shape and size), low-power operation, and high sensitivity required for detecting sound pressures less than 60 dB SPL. Unless the sensor includes any metallic parts, the acoustic sensor 202 can remain implanted in the subject, and would be safe during magnetic resonance imaging (MRI).

Sensor Front-End Circuit

Figure 4B:
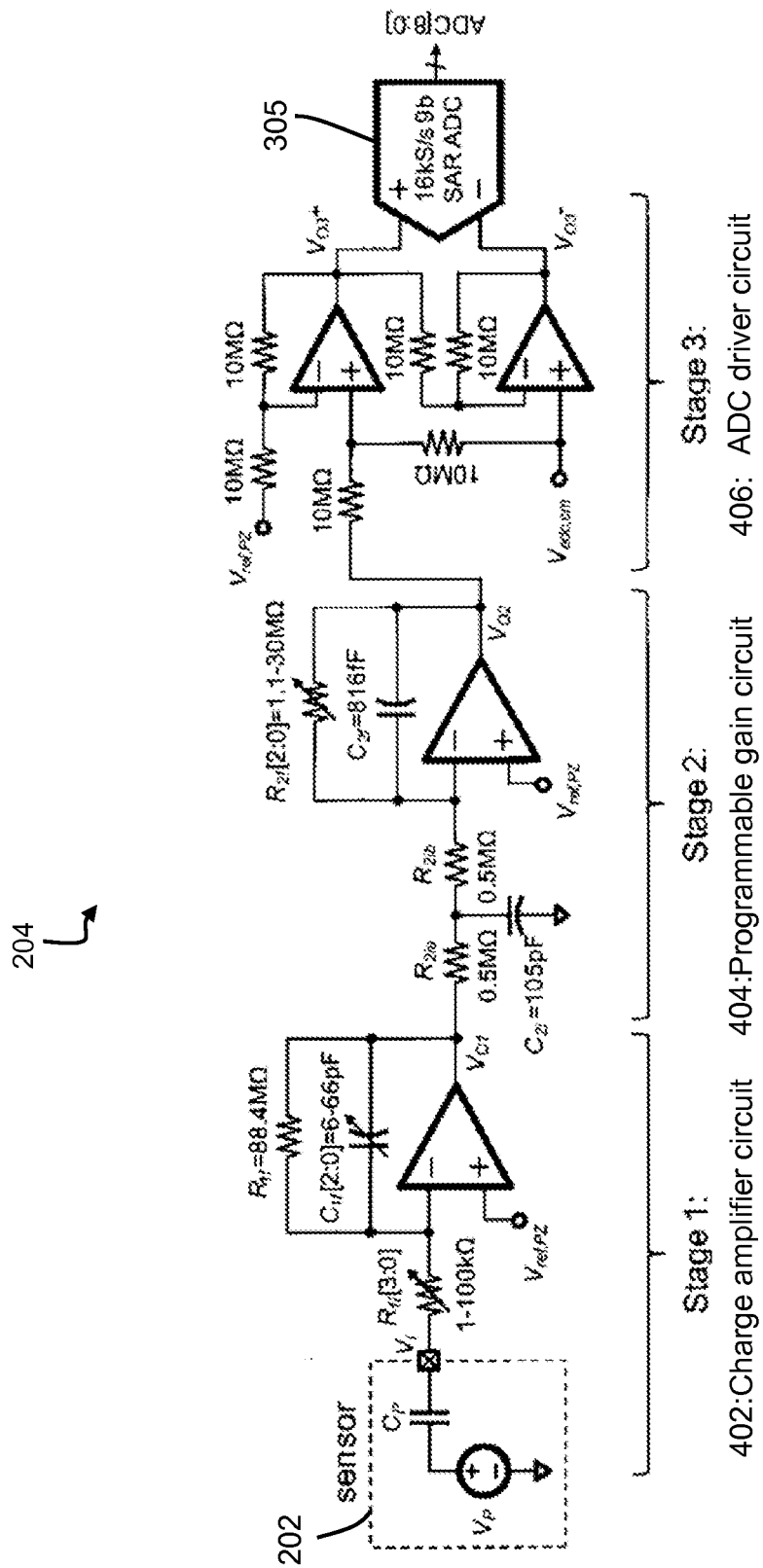
FIG. 4B is a schematic of an example of a sensor front-end circuit.

FIG. 4B is a schematic of an example of sensor front-end circuit 204 that operates from a 1.5 V analog power supply, and includes three stages and an analog-to-digital converter (ADC) 305. Stage 1 includes a charge amplifier 402 that is electrically connected to acoustic sensor 202. Stage 2 includes a programmable gain circuit 404, and stage 3 includes a single-ended to differential ADC driver circuit 406. The sensor front-end circuit 204 provides a mid-rail reference voltage $V_{ref,PZ}$ to bias one terminal (e.g., terminal 413) of acoustic sensor 202. The other terminal (e.g., terminal 411) of acoustic sensor 202 is connected to an input of the charge amplifier circuit 402 as shown in FIG. 4B. The ADC driver circuit 406 provides analog level conversion from $V_{ref,PZ}$=750 mV down to $V_{adc,cm}$=300 mV, which is the input common-mode for ADC 305. In an example, the ADC 305 can be a differential 16 kS/s 9-bit SAR ADC operating from a 0.6 V power supply.

In stage 1, charge amplifier circuit 402 can include resistors $R_{1i}$ and $R_{1f}$, variable capacitor $C_{1f}$, and an operational amplifier (op-amp), e.g., as shown in FIG. 4B. Resistor $R_{1i}$ can be a variable resistor with a resistance value ranging from 1 to 100 kΩ. Acoustic sensor 202 can include a capacitor $C_p$, which can have values from 0.2 nF to 3 nF. Accordingly, $C_{1f}$ can be a tunable capacitor with values small enough (e.g., 6-66 pF) to provide sufficient gain for small values of $C_p$, and large enough to limit the gain for large values of $C_p$ so as not to saturate the charge amplifier circuit 402 response at large sound pressure levels. $C_{1f}$ can be a feedback capacitor being a 3-bit switched-capacitor and is non-uniformly spaced to provide programmable mid-band gain in 3 dB steps. $R_{1f}$ is constrained by the minimum value of $C_f$ and is set to 88.4 MΩ. $R_{1i}$ can be implemented as a 4-bit switched-resistor logarithmically spaced from 1 kΩ to 100 kΩ.

For the acoustic sensor 202 described in relation to FIG. 4A with W=3 mm, L=3 mm, and t=0.5 mm, the minimum signal is about 3 $\mu V_{rms}$ at 40 dB SPL, which sets an upper bound of noise of the sensor front-end circuit 204. The noise from $R_{1i}$ and $R_{1f}$ are reduced for larger values of $C_p$, and the noise from the op-amp can be independent of $C_p$. The noise from $R_{1f}$ is negligible because of its relatively large value of 88.5 MΩ than $R_{1i}$. For $C_p$=0.5 nF and 3 nF as examples, the total noise of the charge amplifier circuit 402 is about 2.5 $\mu V_{rms}$ and 1.7 $\mu V_{rms}$, respectively.

The op-amp in the charge amplifier circuit 402 can be a folded-cascode op-amp with source-degenerated bias transistors to improve noise performance Input devices of the op-amp can be p-type metal-oxide-semiconductor (PMOS) transistors with large pair dimensions to limit 1/f noise so that the op-amp noise is dominated by thermal noise. The op-amp utilizes a common-source stage to increase its open loop gain, and the output of the op-amp is a PMOS source-follower with low output impedance to drive the resistive load of stage 2 of the sensor front-end circuit 204.

For stage 2, the programmable gain circuit 404 can include several resistors, a capacitor, and op-amp, e.g., as shown in FIG. 4B. In this example, $R_{2ia}$ and $R_{2ib}$ are each 0.5 MΩ, $R_{2f}$ is a switch-resistor that is logarithmically spaced between 1.1 and 30 MΩ to provide programmable gain in 6 dB steps from 0.83 dB to 29.5 dB. Capacitor $C_{2f}$ has a value 816 fF. In some implementations, the programmable gain circuit 404 is a 2-pole programmable gain-amplifier (PGA) to provide gain in addition to that of charge amplifier circuit 402. Op-amp of the programmable gain circuit 404 is a cascaded current mirror op-amp to achieve high gain. Its output stage is a PMOS source-follower to provide low output impedance to drive the resistive load by stage 3 of the sensor front-end circuit 204. The noise of the programmable gain circuit 404 can decrease with larger values of $R_{2f}$.

Stage 3 of the sensor front-end circuit 204 includes an ADC driver circuit 406, e.g., as shown in FIG. 4B. In this example, the ADC driver circuit 406 is a single-ended to differential amplifier that is configured to drive the input capacitance of ADC 305, which is about 480 fF. This can be achieved by implementing a series connection of a non-inverting amplifier (e.g., gain=2) and an inverting amplifier (e.g., gain=−1). In this way, the ADC driver circuit 406 can provide an additional gain of 12 dB (4V/V). The two op-amps used in stage 3 are two-stage op-amps that leverage the cascoded current mirror stage of the op-amp in the programmable gain circuit 404, with a high-power common-source output stage to drive the capacitance of ADC 305. Because the ADC 305 operates from a low supply voltage of 0.6 V, stage 3 can provide analog level conversion from $V_{ref,PZ}$=750 mV to the ADC input common-mode of $V_{adc,cm}$=300 mV. This can be achieved by biasing of the feedback network of 10 MΩ resistors.

Sound Processor Circuit

ADC 305 output signals to be received and processed by sound processor circuit 206. Generally, the sound processor circuit 206 can process signals to generate information used to provide electric pulses to a multi-electrode array for stimulating the auditory nerve at different locations. Different electrodes can stimulate different locations so as to emulate the tonotopic structure of the cochlea. Such an approach can be referred as a multi-channel sound processing because the process generates signals for multiple-channels, where each channel corresponds to one electrode of the multi-electrode array. The multi-channel sound processing can utilize, but not limited to, envelope-based strategies, n-of-m strategies, and feature-based strategies.

In this specification, a Continuous Interleaved Sampling (CIS) strategy is utilized as an example. CIS is an example of an envelope-based strategy. In implementing a CIS strategy, each electrode delivers biphasic current pulses in a time-interleaved (non-overlapping) manner relative to other electrodes to minimize channel-to-channel interaction in the cochlea. For a specific electrode, a large amplitude of the current pulse (also referred to as "auditory signals" herein) corresponds to a large amount of energy delivered to the frequency band represented by that specific electrode.

An arrangement of a sound processor circuit 206 utilizing a CIS strategy was described in relation to FIG. 3. As mentioned, detected signal can pass through filter bank 314 that are logarithmically spaced band-pass filters. Each filter in filter bank 314 can correspond to a different spectral channel. An envelope of signals passing each channel can be extracted by extractor 316 by rectification and low-pass filtering. Then the envelope can be compressed by a non-linear function (e.g., logarithmic function) by compressor 318 to scale the dynamic range of acoustic signals to the dynamic range of electrical hearing. The signals processed by sound processor circuit 206 can be used to modulate the amplitude of a train of interleaved current pulses applied to the electrodes. A high rate (e.g., several 100's to 1000's of pulses/s) of stimulation can be achieved with minimal simultaneous channel interaction. This can be advantageous because a high rate of stimulation can preserve temporal information in speech.

Figure 5A:
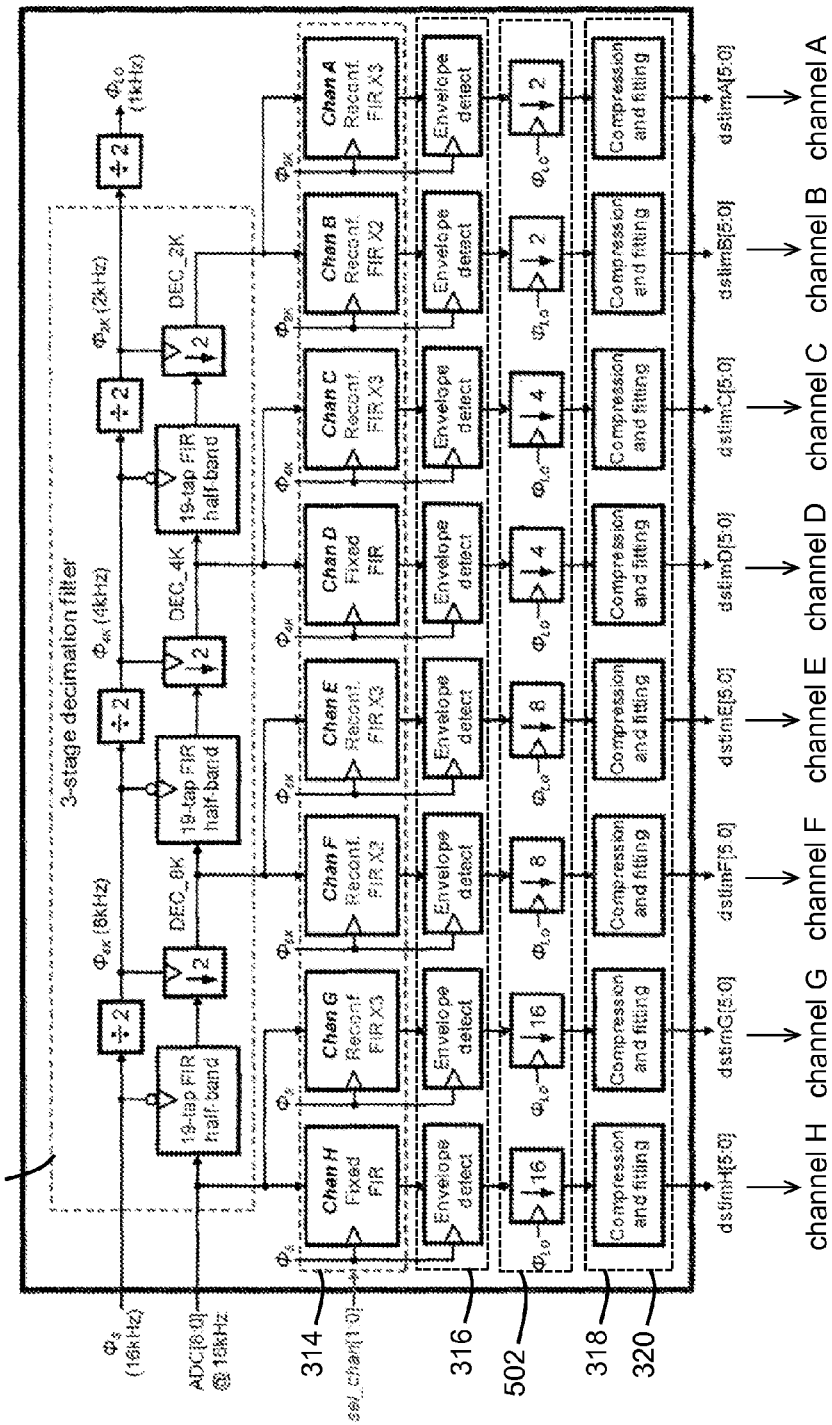
FIG. 5A is a schematic of an example of a sound processor circuit.

FIG. 5A is a schematic of an example of a sound processor circuit 206. In this example, the sound processor circuit 206 is operated by a 0.6 V power supply and has many programmable features. The techniques described herein can allow the sound processor circuit 206 to operate at ultra-low power of 1.90 µW or less and be reconfigurable to balance power and performance with patient specific fitting capabilities. Such features lead to power savings of the overall cochlear implant.

Referring to the example shown in FIG. 5A, electric signals from ADC 305 are input into the sound processor circuit 206 at 16 kHz. A clock signal $f_s$ is input at 16 kHz. A three-stage decimation filter 312 down-samples the clock signal into sample rates of 8 kHz, 4 kHz, and 2 kHz. Accordingly, different samples rates can be set for different channels depending on the configuration of the sound processor circuit 206.

The sound processor circuit 206 can spectrally decompose the input signals from the ADC 305 with a logarithmically spaced filter bank 314 represented as channels A-H in FIG. 5A. Channels A-H represents low to high frequency channels, respectively. In this example, channels A, B, C, E, F, and G are reconfigurable. The number of channels can be reconfigured between 8-, 6-, and 4-channel modes to enable a power-performance tradeoff. For example, subjects (e.g., human patients) can go through a speech recognition test. For some subjects, 4 channels that provide electric pulses to corresponding 4 electrodes may be sufficient for a good speech recognition score, and additional channels may not significantly improve speech recognition. In this case, any channels in excess of 4 channels can be turned off to save operation power of the sound processor circuit 206 at the expense of some resolution of the perceived sound. For some subjects, 6 channels may be sufficient for good speech recognition, and any channels in excess of 6 channels can be turned off to save power.

The number of channels of 4, 6, and 8 are only examples, and any other number of channels can be implemented to fit the needs of different subjects. However, it appears that 8 channels may be more than sufficient in the embodiments described herein. The channels can be logarithmically spaced to emulate the tonotopic structure of hearing.

The sound processor circuit 206 can be configured to operate in 4-, 6-, or 8-channel modes by input signal with 2 bits sel_chan (1:0) sent from a Serial Programming Interface (SPI). For example, when input signal sel_chan(1:0) is data bits 00, the sound processor circuit 206 can operate in 4-channel mode. When input signal sel_chan(1:0) is data bits 01, the sound processor circuit 206 can operate in 6-channel mode. When input signal sel_chan(1:0) is data bits 10, the sound processor circuit 206 can operate in 8-channel mode. The SPI can be included in cochlear implant 200. As the number of channels selected to provide electric pulses to electrodes change, a different subset of channels are selected from channels A-H. In some implementations, bandwidth and center frequency of each filter in filter bank 314 is changed by using FIR filters with 3 levels of reconfigurability in both the coefficients and number of taps of each filter. In certain implementations, bandwidth and center frequency of at least one filter is adjustable.

In some implementations, higher frequency channels of filter bank 314 can have higher bandwidth that that of lower frequency channels of filter bank 314. If the sampling rate for all channels A-H were the same, for example at 16 kHz, the lower frequency channels would need higher order filters (e.g., more taps in an FIR filter), which increases both power consumption and occupied area of the filters. To avoid this, multi-rate signal processing can be used, where the lower frequency channels operate at low sample rates, while higher frequency channels operate at higher sample rates. This can allow each filter to provide its bandwidth with optimum filter order without excess power consumption and occupied area. To achieve this, the sampling rates 2 kHz, 4 kHz, 8 kHz, and 16 kHz provided by 3-stage decimation filter 312 are sent to respective low and high frequency channels.

In the example shown in FIG. 5A, channels A-H represent low to high frequency channels, and channels A/B, C/D, E/F, and G/H operate at a sampling rate of 2 kHz, 4 kHz, 8 kHz, and 16 kHz, respectively. In this embodiment, the decimation filter 312 uses 19-tap half-band FIR filters to perform anti-aliasing.

Generally, filters of filter bank 314 can be implemented with FIR filters or Infinite Impulse Response (IIR) filters, which can be more hardware efficient. FIR filters can operate with linear phase, in other words constant group delay, which can have a positive effect on sound quality and speech intelligibility. In addition, FIR filters can have unconditional stability and regular structure, which allows for easy design. Referring to FIG. 5A, when sound processor circuit 206 is configured to operate in an 8-channel mode, all channels A-H are active. When sound processor circuit 206 is configured to operate as a 6-channel mode, channels D and H are clock-gated and turned off, and channels A-C and E-G map as channels 1 to 6, respectively. When sound processor circuit 206 is configured to operate in a 4-channel mode, channels B, D, F, and H are clock-gated and turned off, and channels A, C, E, and G are mapped to channels 1 to 4, respectively. Filters of the filter bank 314 can be reconfigured depending on the channel mode so that the cut-off frequencies of the individual filters can be adjusted depending on the channel mode.

Figure 5B:
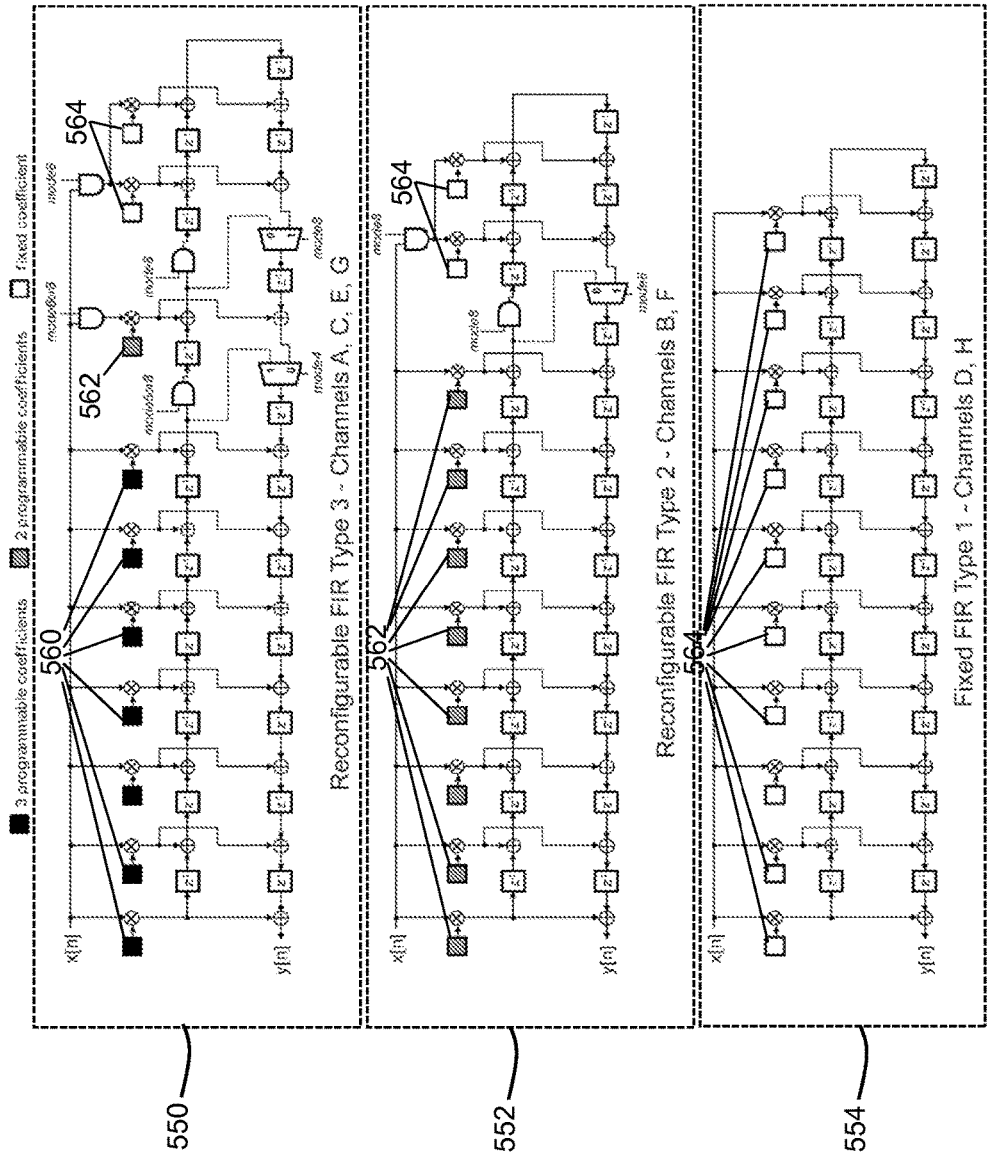
FIG. 5B is a schematic showing three different types of Finite Impulse Response (FIR) filters used in a filter bank.

Regardless of the channel mode, sound processor circuit 206 can cover a bandwidth from 300 Hz to 5.5 kHz. The reconfigurability of the filter bank 314 are achieved by implementing three types of FIR filters with different levels of reconfigurability as described in relation to FIG. 5B. FIG. 5B is a schematic showing three different types of FIR filters used in filter bank 314. Coefficients (also referred as "coefficient signals") labeled as reference number 560 can be chosen from three values, coefficients labeled as reference number 562 can be chosen from two values, and coefficients labeled as reference number 564 have one fixed value. The number of taps in each filter increases with the number of channels for more selectivity. x[n] is the input of signal received from ADC 305, and y[n] is the filtered output sent to extractor 316. Coefficient signals are also input to the filters for multiplication to x[n].

Filter 550 is the most reconfigurable filter (also referred as FIR X3) among the three types. Filter 550 can be programmed to three different filter lengths: 14-, 16-, or 20-taps used in the 4-, 6-, or 8-channel mode, respectively. Filter 550 is used for channels A, C, E, and G in all 4-, 6-, or 8-channel mode. Filter 552 is also referred as FIR X2 filter, which is used for channels B and F, and can be programmed to two different filter lengths: 16- or 20-taps used in the 6- or 8-channel modes, respectively. Filter 552 is clock-gated when the sound processor circuit 206 operates in the 4-channel mode. Filter 554 is a 20-tap FIR filter used for channels D and H, and is fixed and used in the 8-channel mode. Filter 554 is clock-gated during operation in 4- or 6-channel modes. In some implementations, clock-gating is applied to channels that are not selected and turned off. This approach reduces the number of channels and saves power consumption of the cochlear implant.

Digital circuits such as the filters can draw power when the filters receive rising edges of input clock signals. Therefore, filters of channels that are not being used can still consume power if such filters receive the clock signals. To reduce power consumption, the filters that are not being used can be clock-gated. For example, clock-gating a filter can be achieved by sending a clock signal and a logic turn/off signal into an AND gate, and then sending the output of the AND gate to the filter. When the filter is not being used, a logic off signal is sent to the AND gate so that its output is zero (off). The filter receives a zero signal and does not draw power. On the other hand, when the filter is to be used, a logic on signal is sent to the AND gate so that its output is the clock signal, which is received by the filter for operation.

Another scheme to save power is to use symmetric coefficients for filters 550-554. When using symmetric coefficients, the filters can be folded so that a pair of filters can use the same multiplication (indicated by "×" with outer circle in FIG. 5B). Hence, the number of multiplications of coefficients and input x[n] can be reduced by half so that power consumption is reduced.

Moreover, filter word lengths can be optimized for the given filter coefficients. For example, the coefficients can be quantized to 8-bit precision, which can be the minimum without significantly affecting the frequency response. In this way, the coefficients do not need to be higher precision (e.g., 9-bit or more) so as to save power—multiplication using higher precision can lead to more power consumption. The filters can be implemented in transposed form so that there is at most one adder in their critical path.

Referring back to FIG. 5A, signals filtered by filter bank 314 are passed through extractor 316, which extracts the envelope of the signals for each channel rectifying the signals and then passing through a low-pass filter. An input logic signal can be used to select whether the rectification type is a full-wave or half-wave rectification. The low-pass filter can have a cut-off between 50 Hz to 500 Hz. For example, the low-pass filter can be a $2^{nd}$-order Butterworth filter with a 400 Hz cut-off used to limit the bandwidth of extracted envelopes before being down-sampled as an output with data rate of 1 kHz by passing through down-sampler 502. The output of each channel can be a 6-bit value.

The extracted envelope and down sampled signals provided by the extractor 316 and down-sampler 502 can be passed onto compressor 318. In FIG. 5A, the optional fitting circuit 320 is depicted together with compressor 318 as one block component. When signals pass through compressor 318, a channel gain applied to all channel can be applied from $2^{-4}$ to $2^3$. In some implementations, the signals can be logarithmically compressed in amplitude according to Eq. (2):

$$Y = \frac{\ln(1 + CX)}{\ln(1 + C)} \quad (2)$$

where X is the input, Y is the output, and C is the compression factor. Logarithmic compression can be applied to take account of the loudness growth function of electrical hearing that describes the linear relationship between acoustic sound intensity in decibel (dB) sound pressure level (SPL) and electric stimulation intensity in amperes. The value of C can be variable to accommodate different amounts of compression, which may be used for different subjects. For example, C can be 1024, 128, and 16. Generally, C can be other values and selected to be specific to a subject. For example, the value of C can be selected by adjusting the value while testing how the subject perceives the sound. In some implementations, compression functions with different C values can be stored in the sound processor circuit 206 as look-up tables, for example, each with 512 6-bit wide values.

For each channel, the compressed signals output from compressor 318 can pass through a fitting circuit 320. The fitting circuit 320 can be used during an audiology fitting session to adjust the dynamic range between the minimum and maximum current level for each electrode corresponding to the respective channel to ensure a patient specific fit for individual threshold (THR) and most-comfort able-level (MCL) settings. The THR can be a threshold level that the patient starts to perceive sound. The MCL can be the level that the patient perceives the level of sound as being most comfortable for listening. Each channel can have a 3-bit programmability for both THR and MCL. As shown in FIG. 5A, outputs of the sound processor circuit 206 are dstimA [5:0] to dstimH[5:0] corresponding to channels A to H, respectively. Each output is updated at a rate of 1 kHz and sent to waveform stimulator 208, which can be used to modulate a train of current pulses, for example, at 1000 pulse/s per electrode).

Each output from the channels of sound processor circuit 206 is the compressed temporal envelope of signals at the particular frequency band of the respective channel. The envelope can be used to determine the strength of the stimulus delivered to corresponding electrodes of electrode array 210.

Waveform Stimulator and Electrode Array

Figure 6:
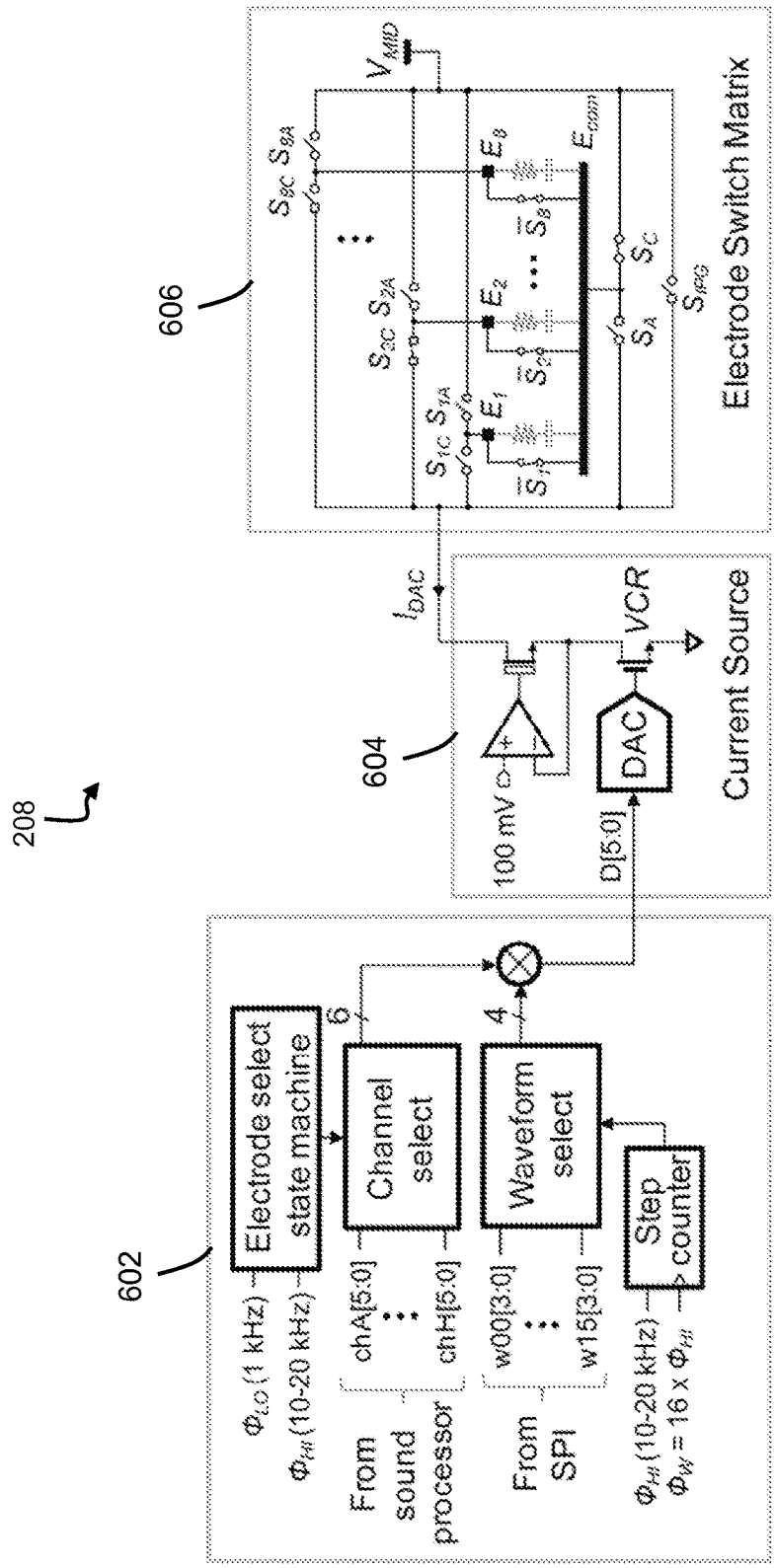
FIG. 6 is a schematic of an example of a waveform stimulator circuit.

Waveform stimulator 208 can include a digital waveform interface circuit 602, current source 604, and electrode switch matrix 606 as schematically shown in FIG. 6. Implementing the CIS strategy allows the use of a single (only one) current source 604 to provide electrical pulses to all electrodes of electrode array 220. The electrical pulses can be sequentially applied using electrode switch matrix 606 to activate an electrode and control the direction of current flow. A common return electrode can be used as the return path for all electrodes. The digital waveform interface circuit 602 can be used to provide a shape of the waveform of the electrical pulses passing through the activated electrodes. Parameters (e.g., shape, pulse-width) can be loaded to the digital waveform interface circuit 602 through a serial programming interface (SPI). The digital waveform interface circuit 602 can provide control signals for the electrode switch matrix 606.

Figure 7A:
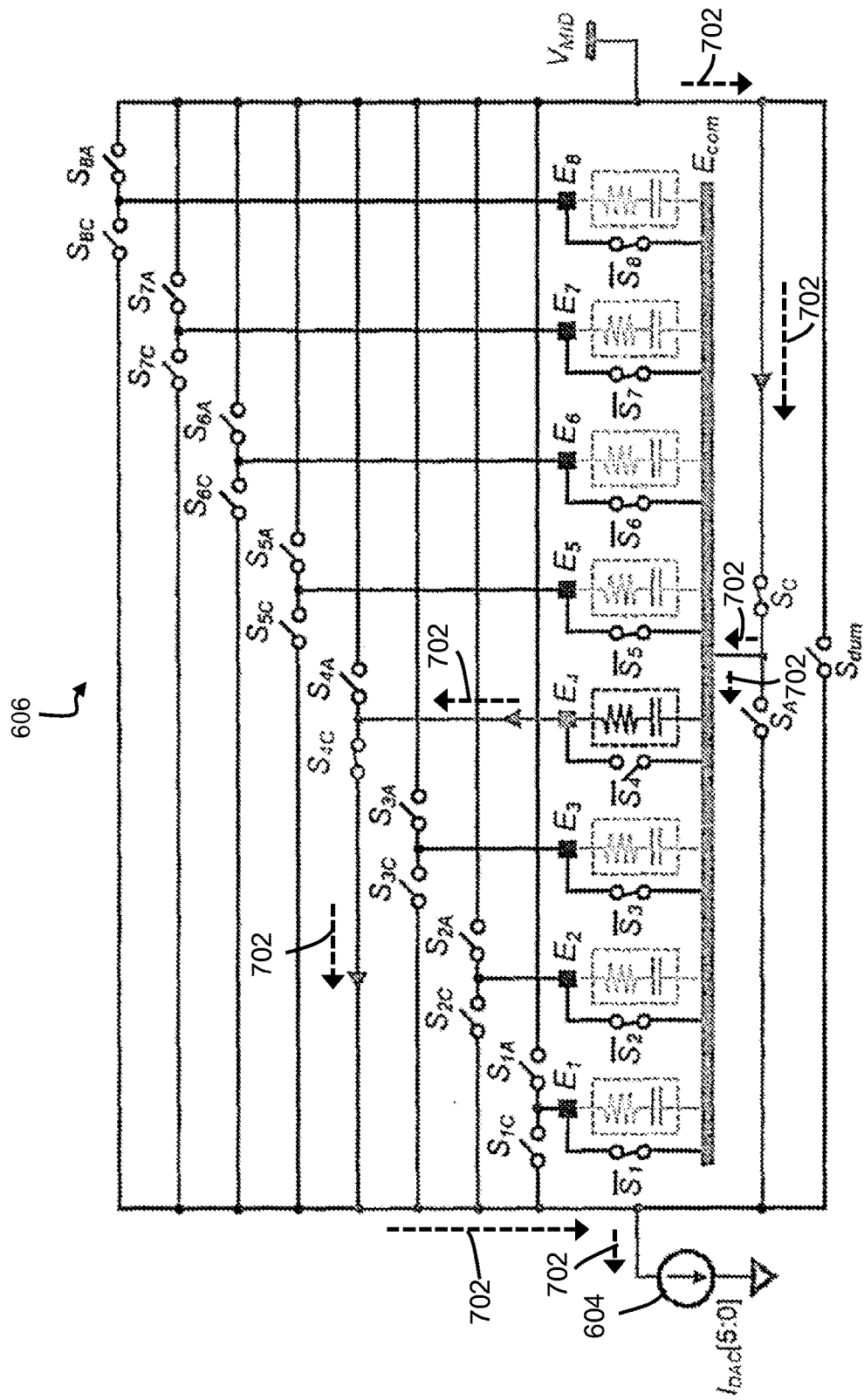
FIGS. 7A and 7B are schematics of an example of an electrode switch matrix.
Figure 7B:
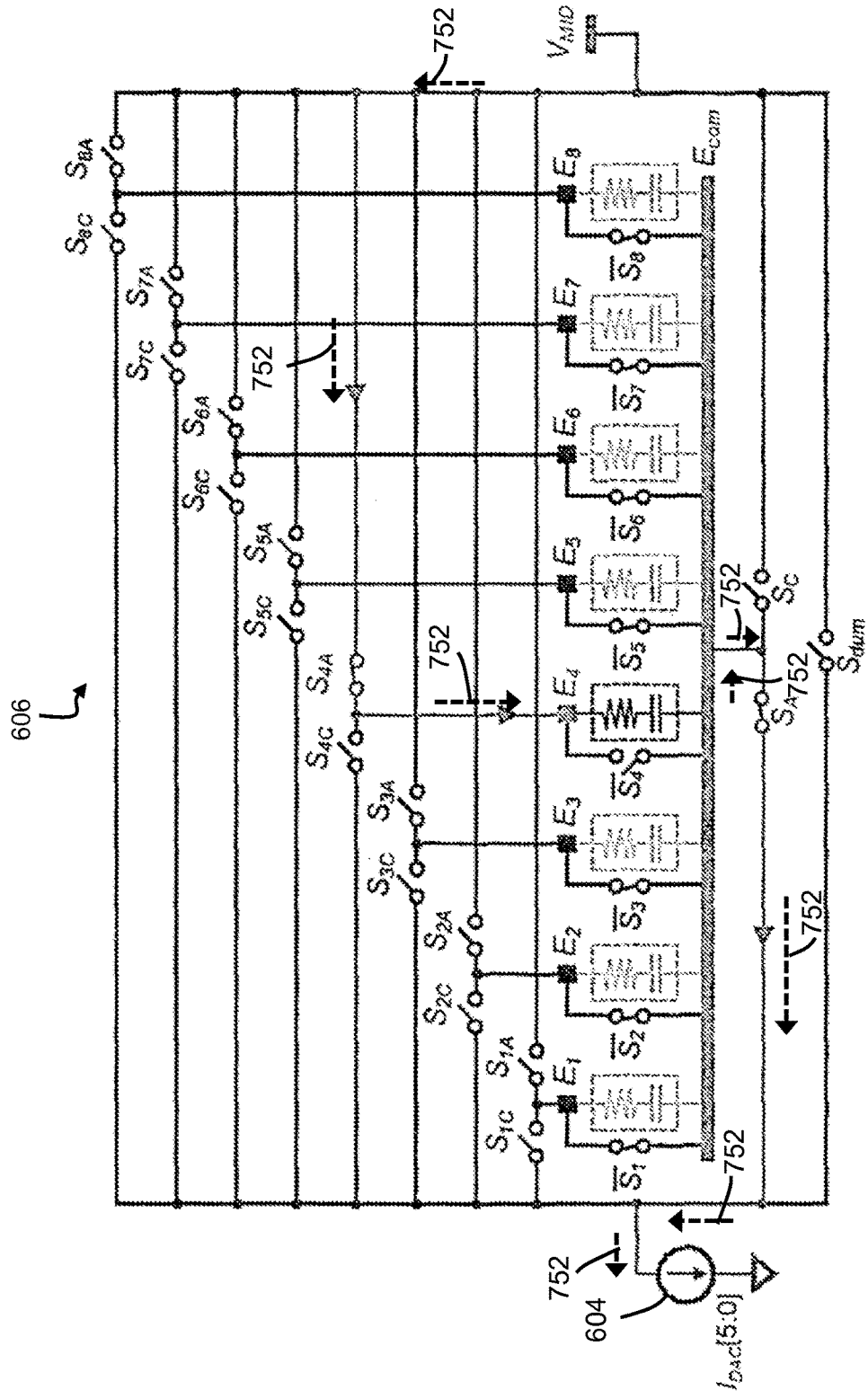

In some implementations, a single current source 604 can provide currents to multiple electrodes of electrode array 210 through electrode switch matrix 606 (e.g., high-voltage electrode switch matrix). The electrode switch matrix 606 can control which electrode is selected to apply the current supplied by current source 604. To describe the operation of the electrode switch matrix 606, FIGS. 7A and 7B show schematics of electrode switch matrix 606 operating during cathode phase and anodic phase, respectively, of pulses applied to electrodes. In these figures, electrodes $E_i$ (i=1 to 8) represent the intracochlear electrodes of electrode array 210, and $E_{com}$ is the common return electrode. Switches $S_c$, $S_A$, $S_{iC}$, and $S_{iA}$ are used to select the active electrode ($E_i$) and control the direction of current flow. Electrode $E_i$ is active when its corresponding $S_{ic}$ or $S_{ia}$ is closed. In FIGS. 7A and 7B, electrode $E_4$ is the active electrode.

Referring to FIG. 7A, electrode switch matrix 606 provides the cathodic phase of a stimulation pulse through $E_4$ when $S_c$ and $S_{4C}$ is closed (i.e., turn on). Dash arrows 702 show the direction of current flow. The current flows negatively through $E_4$ from $V_{MID}$, which is a voltage supply (e.g., high voltage supply of 5-10 V). The strength of the current is determined by the current source 604. In this example, the current source 604 is a 6 bit source ($I_{DAC}$ [5:0]), which is described in detail later. Referring to FIG. 7B, electrode switch matrix 606 provides the anodic phase of stimulation pulse through $E_4$ when $S_c$ and $S_{4C}$ is open (turned off) and $S_A$ and $S_{4A}$ is closed. The current direction in electrode $E_4$ is reversed as indicated by dash arrow 752. The electrode switch matrix 606 works as an H-bridge and current flows from $V_{MID}$ towards ground of current source 604.

During each of the cathodic and anodic phases, digital waveform interface circuit 602 controls current source 604 to provide a controlled waveform shape of electric pulses pass through the active electrode in electrode switch matrix 606. In between cathodic and anodic phases of a given pulse, an optional switch $S_{dum}$ (also referred as $S_{IPG}$) can be used to insert an inter-phase gap. After the completion of each pulse, switch $\overline{S}_i$ is turned on to short electrode $E_i$, which was active, to ensure that residual charges are depleted. In some implementations, a DC blocking capacitor (e.g., with capacitance of 220 nF) can be placed in series with the electrodes so that no DC current flows to the nerve fiber for safety.

Various switches of electrode switch matrix 606 can be controlled using several clocks. For example, several non-overlapping clocks and control signals can be used to generate on-off signals for switches $S_c$, $S_a$, $S_{iC}$, $S_{iA}$, and $S_{dum}$. An example is described in relation to FIG. 5-13 of U.S. Provisional Application 61/908,237 filed on Nov. 25, 2013, the entire contents of which are incorporated herein by reference.

Referring back to the example shown in FIG. 6, current source 604 includes an op-amp, digital-to-analog converter (DAC), and voltage-controlled resistor (VCR). The DAC receives data signal from digital waveform interface circuit 602 described later. The DAC can operate by a 3.3 V power supply and leverage current steering to achieve fast settling for generating arbitrary waveforms with a short time step. For example, the time step can be 2.5 μs to provide a phase width of 25 μs with 10 steps/phase. Input code D[5:0] from the digital waveform interface circuit 602 can steer binary-weighted currents. The VCR can have a large output impedance and high voltage compliance. High output impedance is used so that the current delivered to the electrodes do not depend on the electrode impedance. High voltage compliance is used for high efficiency and to avoid saturation of the current source 604 when the electrode impedance and the delivered currents are high. In some implementations, the current source 604 can provide 6 bit resolution of current strengths supplied through electrodes. The high resolution can lead to various shapes as well as amplitudes of waveform of the electric pulses provided to the electrodes. In some implementations, multiple current sources can be used to provide the functions described in relation to current source 604.

In some implementations, current source 604 can achieve fast settling to generate electrical pulses having waveforms with short time steps. FIG. 7C is a schematic of an example of waveform 770 of an electrical pulse generated by current source 604. X-axis is time and y-axis is current. In this example, during time duration $t_1$, the current source 604 provides current at amplitude 772. The current source 604 can change the current amplitude by an amount 774 so that during time duration $t_2$, the current source 604 provides current at the sum of amplitudes 772 and 774. Time durations $t_1$ and $t_2$ can be referred as a time step of the waveform. The time step can be 5 μs or less (e.g., 4 μs or less, 3 μs or less, 2.5 μs or less, 2 μs or less, 1 μs or less). By changing the current amplitude for different time steps, the current source 604 can provide an arbitrary waveform. As the time step becomes smaller, the current source 604 has more time resolution to provide a waveform resembling a smooth and continuous waveform. In some implementations, the current source 604 can vary the current amplitude within short times scales (e.g., within time duration $t_1$). For example, the current source 604 can change the current amplitude by 0.5 mA or more (e.g., 0.6 mA or more, 0.7 mA or more) within one time step. Such fast adjustment of current amplitudes can be achieved by fast settling capabilities of the current source 604.

In the example illustrated in FIG. 7C, pulse width 780 corresponds to the cathodic phase and pulse width 782 corresponds to the anodic phase of the waveform 770. Accordingly, the cathodic phase has 6 steps/pulse and the anodic phase has 6 steps/pulse. Generally, the cathodic and anodic phases can have different numbers of steps/pulse.

Figure 7D:
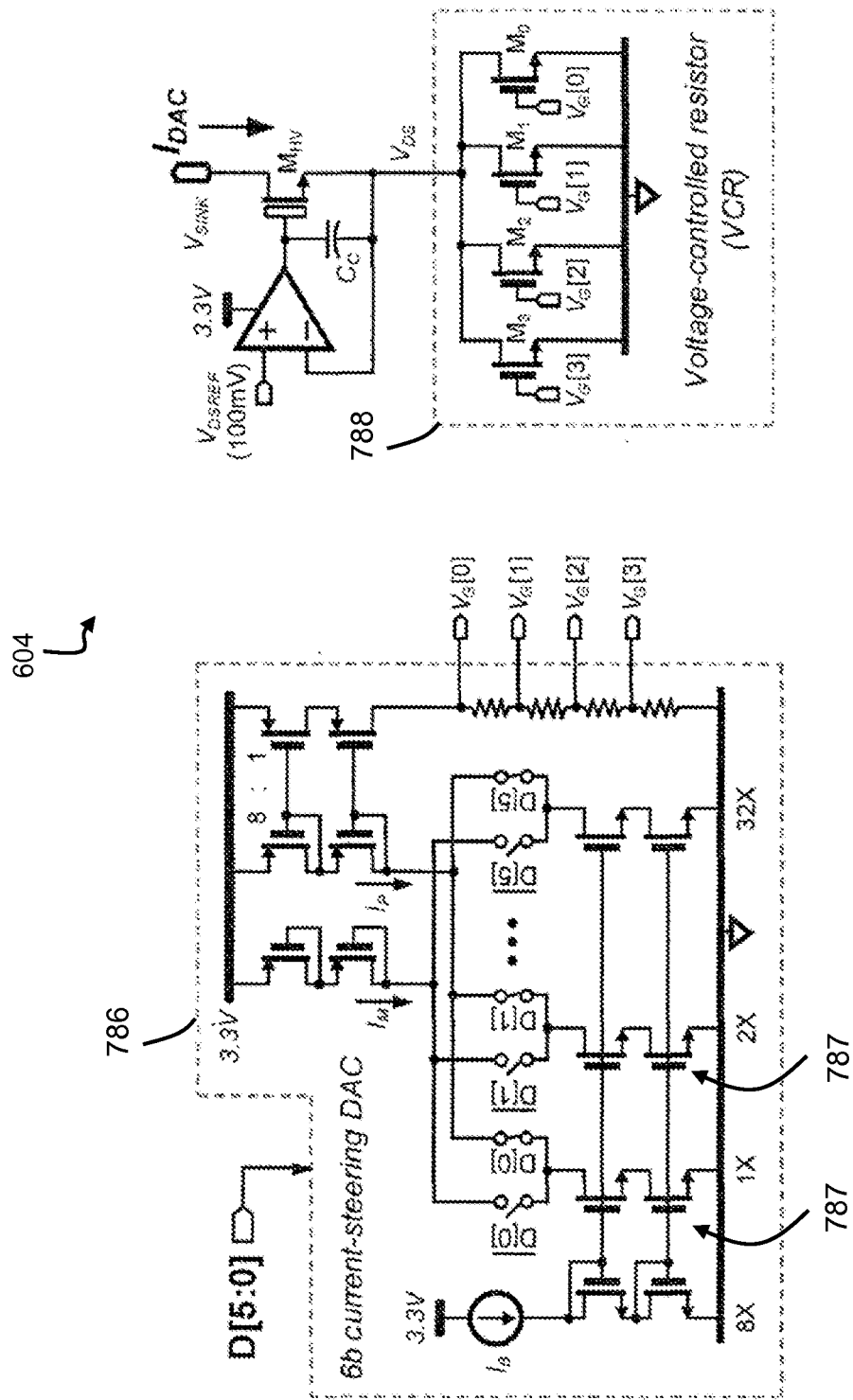
FIG. 7D is a schematic of an example of a current source circuit.

FIG. 7D is a schematic of an example of a current source 604 that provides fast settling as described in relation to FIG. 7C. The current source 604 can include a DAC 786 and a voltage-controlled resistor (VRC) 788. The DAC 786 can be a 6-bit resolution DAC that provides voltages $V_G$[0]-[3] to control the VCR 788. The DAC 786 can leverage current steering to achieve fast settling to generate arbitrary waveforms. The input data signal D[5:0] from digital waveform interface circuit 602 can steer binary-weighted currents to $I_p$ that is then mirrored to output branch. A resistor string can convert current $I_p$ (dependent on D[5:0]) into the control voltages $V_G$[0]-[3]. In some implementations, the DAC 786 can have cascoded transistors 787 that have a constant current flowing through cascaded transistors 787 so as to enable fast steering of currents between $I_m$ and $I_p$ depending on D[5:0]. $I_p$ can be continuously flowing from supply (e.g., 3.3V supply) during operation of the current source 604 so that fast switching of voltages $V_G$[0]-[3] can be achieved. This aspect can lead to the fast settling feature of the current source 604.

The current source 604 can be operated from a 3.3V supply. The current source 604 can use a feedback to force a reference voltage $V_{DSREF}$ across VCR 788 with value $R_{VCR}$. The output current can be expressed as Eq. (3):

$$I_{DAC} = \frac{V_{DS}}{R_{VCR}} = \frac{V_{DSREF}}{R_{VCR}} \quad (3)$$

where $V_{DS}=V_{DSREF}$ through a virtual short as long as the loop gain is high. $R_{VCR}$ of VCR 788 can be varied to adjust $I_{DAC}$, which corresponds to the current amplitude described in relation to FIG. 7C. The VCR 788 can include a bank of n-channel metal-oxide-semiconductor (NMOS) transistors that collectively provide a linear resistance. In this example, $R_{VCR}$ is a function of gate voltages $V_G$[0]-[3] provided by DAC 786. $M_o$ can be the main triode device that carries the majority of $I_{DAC}$ being controlled by $V_G$[0]. $M_1$ to $M_3$ can be auxiliary devices controlled by $V_G$[1]-[3]. $V_{DSREF}$ can be set to 100 mV so that $M_o$ is a triode device and to limit the headroom of the current source 604 to achieve high compliance.

As mentioned earlier, digital waveform interface circuit 602 can be configured to provide a shape of the waveform of the electrical pulses provided by current source 604. FIG. 6 shows a schematic of an example of the digital waveform interface circuit 602. The digital waveform interface circuit 602 includes an electrode select state machine, channel select circuit, waveform select circuit, and step counter. The electrode select state machine receives clock $f_{LO}$ and $f_{HI}$, and generates signals for switches of S1 to S8 of electrode switch matrix 606 and passes onto channel select circuit. The electrode select state machine can receive control signals used to reconfigure the state machine between 4-, 6-, and 8-channel modes.

The channel select circuit can receive the data signal dshmA[5:0] to dshmH[5:0] (also labeled as chA[5:0] to chH[5:0]) from sound processor circuit 206. The channel select circuit can choose the data signal of the corresponding electrode that is activated by the electrode state select machine, and use the chosen data signal to determine the strength of electric pulses to be applied by current source 604 for the activated electrode. On the other hand, the waveform select circuit can receive input parameters w00[3:0] to w15[3:0] of the waveform to be generated from an SPI. The waveform select circuit provides the waveform shape to current source 604. Parameters w00[3:0] to w15[3:0] can be multiplied to chA[5:0] to chH[5:0] to generate output D[5:0], which is the input to current source 604.

In this way, output (dstimA[5:0] to dstimH[5:0]) of sound processor circuit 206 can modulate the amplitude of stimulus pulses, while the shape of the pulses are determined by height of the pulse, which has an arbitrary waveform shape determined input parameters w00[3:0] to w15[3:0] from SPI. In the example shown in FIG. 6, w00 to w03 specify the shape of the cathodic phase, and w04 to w07 specify the shape of the anodic phase. The multiplication of a set of parameters w00 to w15 can be carried out for each channel sequentially. Step counter counts the number of steps per pulse. The total number of steps can be 8 steps/pulse (e.g., 16 steps/pulse).

In some implementations, the total number of steps can be adjusted. Frequency of $f_{HI}$ and $f_W$ can be tuned to vary the phase width and number of step/phase, respectively, of the waveform to be generated.

In some implementations, the digital waveform interface 602 can control the waveform so that the charge delivered to the nerve fiber during the cathodic phase within 5% or less (e.g., 3% or less, 1% or less) of the charge delivered during the anodic phase. The waveform stimulator 208 can utilize DC blocking capacitors and a shorting phase so that no or negligible DC current is delivered to the nerve fiber for safety.

In some implementations, the digital waveform interface circuit 602 can operate at 0.6 V to save power consumption. Accordingly, a two-stage level shifter can be used between the low-voltage (e.g., 0.6 V) digital domain and the high-voltage (e.g., 7V to 12V) domain of the electrode switch matrix 606. The two-stage level shifter can be used so that the low-voltage domain and the high voltage domain are compatible with each other. For example, an intermediate voltage of 1.8 V can be used in the two-stage level shifter between the 0.6 V power supply and high (e.g., 7 V to 12V) voltage power supply. An example is described in relation to FIG. 5-15 of U.S. Provisional Application 61/908,237 filed on Nov. 25, 2013, the entire contents of which are incorporated herein by reference.

Power supplies providing power at 1.0 V or less can be used in cochlear implant 200 to power various components and to provide the required nerve stimulation. In some implementations, the power supply can provide power at less than 0.6 V. For example, a lower power (e.g., 0.6 V) supply can be used so as to operate the component close to the component's minimum energy point of energy dissipation within 10% (e.g., within 5% or within 3%) to maximize energy efficiency of the component's operation. Scaling the power supply voltage of digital circuits down to moderate inversion slightly above their threshold can provide a good balance between digital energy efficiency and performance bandwidth. On the other hand, power consumption of analog circuits can be a complex function of factors such as dynamic range, gain-bandwidth, topology, and supply voltage. Digital processing at 0.6 V can be used to leverage the benefits of voltage scaling of digital circuits.

Figure 17:
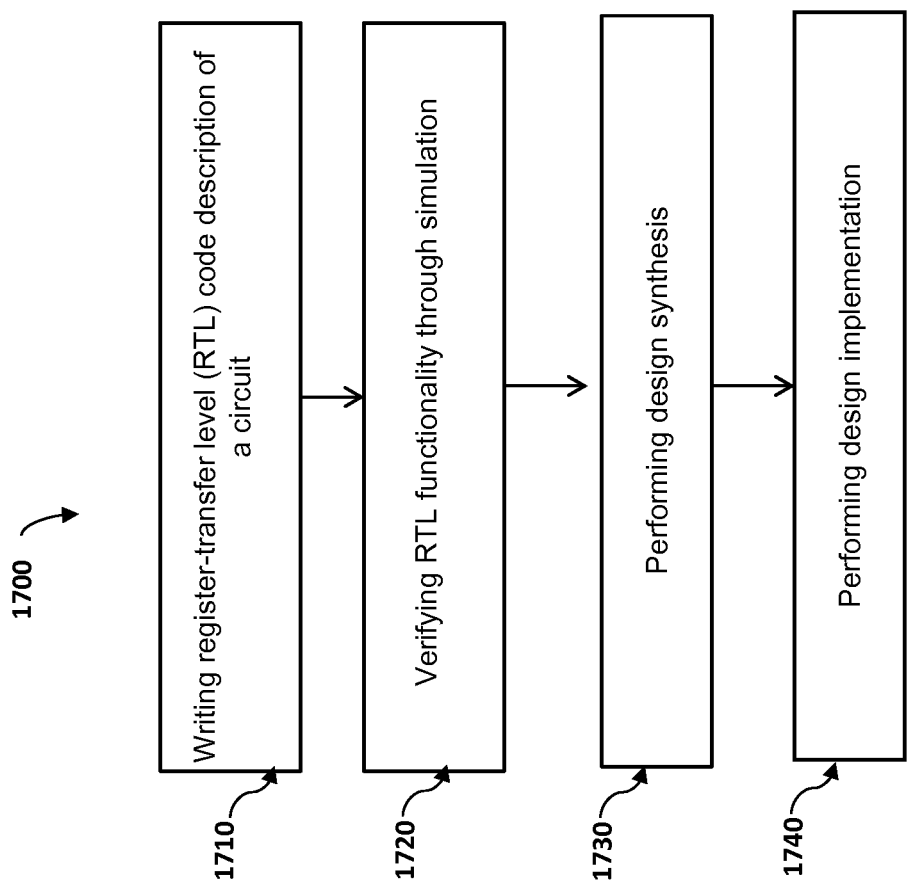
FIG. 17 is a flow chart depicting exemplary operations for designing a circuit that operates from a power supply providing 1.0 V or less.

Flow chart 1700 in FIG. 17 depicts examples of operations for designing a circuit that operates from a power supply providing 1 V or less (e.g., 0.6 V). Operations can include writing register-transfer level (RTL) code description of a circuit (1710). Operations can also include verifying functionality through simulation of the circuit (1720). Design synthesis can be performed through logic optimization, map to technology, and adding timing and area constraints of components of the circuit (1730). Operation 1730 can be performed at a nominal voltage technology (e.g. 1.8V for a 180 nm complementary metal-oxide-semiconductor technology) with the nominal technology library and add significant timing margins so that the circuit can operate at a low voltage such as 0.6V. In another approach, operation 1730 can be performed by re-characterizing the technology library at 0.6 V and running the design synthesis with the re-characterized technology library. Operations can further include performing design implementation: floor planning and checking function, timing, place and route, and physical layout. These operations can be used to design power supply voltage, clock frequency, and threshold voltage of the circuit so as to operate at its minimum energy point dissipation.

Generally, cochlear implant 200 can be powered by a battery 212 (e.g., rechargeable battery). In some implementations, a wireless power delivery scheme can be used to charge an ultra-capacitor or battery that supplies power for operation of various components of cochlear implant 200. Utilizing a wireless power delivery and storage scheme can enable untethered usage for a full day, and eliminate the need for an external power unit. The battery 212 can be recharged when a subject is in a specific location for a length of time, e.g., asleep, at a desk, while watching television, or is otherwise at rest.

Reconfigurability and programmable capability of cochlear implant 200 are designed to provide scalability of stimulation power, which can lead to power saving schemes. For example, in some implementations, power consumption of sound processor circuit 206, current source 604, and stimulation power can scale linearly with the number of operating channels. This can be achieved by clock-gating digital circuits and power-gating analog circuits (e.g., current source) when not in use. Clock-gating was previously described in relation to reconfigurable filters. Power-gating of an analog circuit can be achieved, for example, by using a transistor between power supplies that supply power to the analog circuit. The transistor can receive an on/off signal that controls whether power is supplied to the analog circuit.

For example, when an "on" signal is input to the transistor, power can be applied from the power supply to the analog circuit. By controlling the transistor so that the analog circuit does not receive power when the analog circuit is not in use power consumption can be reduced. In some implementations, digital circuits and analog circuits can send/receive handshake signals to each other to control the respective clock-gating and power-gating during operation of the overall circuits.

General Methodology

The techniques disclosed in this specification provide methods for generating energy-efficient stimulation waveforms for significantly reducing the stimulation power needed to operate a cochlear implant 200. In some implementations, the cochlear implant 200 can provide biphasic electrical neural stimulation waveforms that are more energy-efficient than conventional waveforms (e.g., rectangular waveforms). The energy-efficient waveforms can be generated by SPI and digital waveform interface circuit 602 as described herein.

Figure 8:
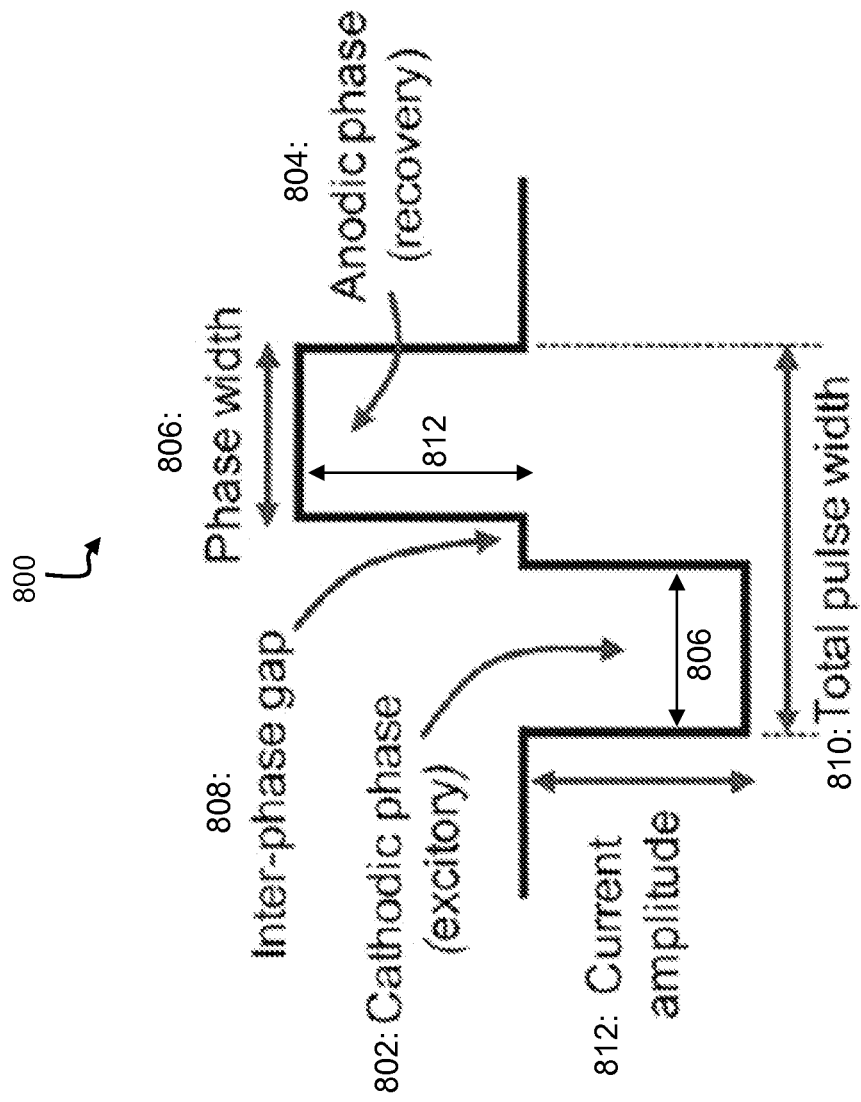
FIG. 8 is a schematic of a conventional waveform.

FIG. 8 is a schematic of a conventional waveform 800 applied to an electrode for stimulation. Waveform 800 includes a cathodic (excitory) phase 802, which is depolarizes a nerve fiber, followed by an anodic (recovery) phase 804, which is applied so that no net charge is delivered to the nerve fiber. The cathodic phase 802 precedes the anodic phase 804. In FIG. 8, both cathodic and anodic phases 802 and 804 have same phase width 806 and same current amplitude 812. The two phases 802 and 804 are separated by an inter-phase gap 808 so that the total pulse width 810 is the sum of two phase width 806 and the inter-phase gap 808. During the cathodic phase 802, the chip delivers charge from the electrode to the nerve fiber in one direction, and during the anodic phase 804, charge is delivered in the reverse direction.

The waveform 800 can also be referred as a "biphasic rectangular current pulse," because of the rectangular shapes of the cathodic and anodic phases 802 and 804. Such a waveform has been used for its simple shape and ease of generation, and was assumed to be optimum for charge-balancing and minimizing the energy consumed under the constraint of delivering equal charge. However, the threshold for neural activation is a function of waveform shape, and activation of a neural fiber can be achieved with different amounts of charge injection depending on the waveform shape. Accordingly, the techniques disclosed herein provide methods for determining and generating alternate waveforms differing from conventional waveform 800 to achieve the same level of neural activation while reducing the amount of energy consumed in generating the alternate waveforms.

A cochlear implant 200 can include an electronic processor that calculates and determines a waveform to be used for providing stimulus pulses by the cochlear implant 200 to a neural fiber. In some implementations, the electronic processor is external and not included in the cochlear implant 200, and can send the determined waveform parameters to the cochlear implant 200. For example, the electronic processor can be included in a computer system of a clinical lab. The electronic processor can be configured to send the determined waveform parameters to the cochlear implant 200 via an SPI as described earlier.

The electronic processor can calculate a waveform once and the parameters of the waveform can be saved in the cochlear implant 200. For example, the parameters can be saved in waveform stimulator 208. The parameters can be saved in a memory of the cochlear implant 200. In this way, the waveform does not need to be calculated every time the waveform stimulator 208 generates electrical stimulus pulses based on the waveform but rather use the same waveform over repeated generation of pulses. In some cases, the electronic processor can recalculate a new waveform that is saved in the cochlear implant 200. The recalculation can be periodically done without user input or can be prompted by a person (e.g., the subject or clinician). In some implementations, the SPI described in preceding sections can calculate and determine the waveform in a similar manner described in relation to the electronic processor.

In some implementations, the electronic processor can calculate the energy of a waveform as defined as the energy per unit resistance ($\bar{E}_{elec}$) in the electrode of the phase width (PW) according to Eq. (4):

$$\bar{E}_{elec} = \frac{E_{elec}}{R_{elec}} = \oint_{<PW>} I^2(t)dt \qquad (4)$$

where I(t) is the current of the waveform, PW is pulse width, $E_{elec}$ is the total waveform energy, and $R_{elec}$ is the electrode resistance, assuming there is no energy wasted by headroom of current source 604.

Figure 9B:
FIGS. 9A-C are schematics of a computational model used for calculating a trigger of action potential for various stimulus waveforms.
Figure 9C:
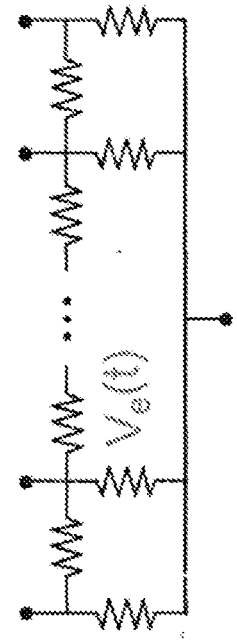
Figure 9A:
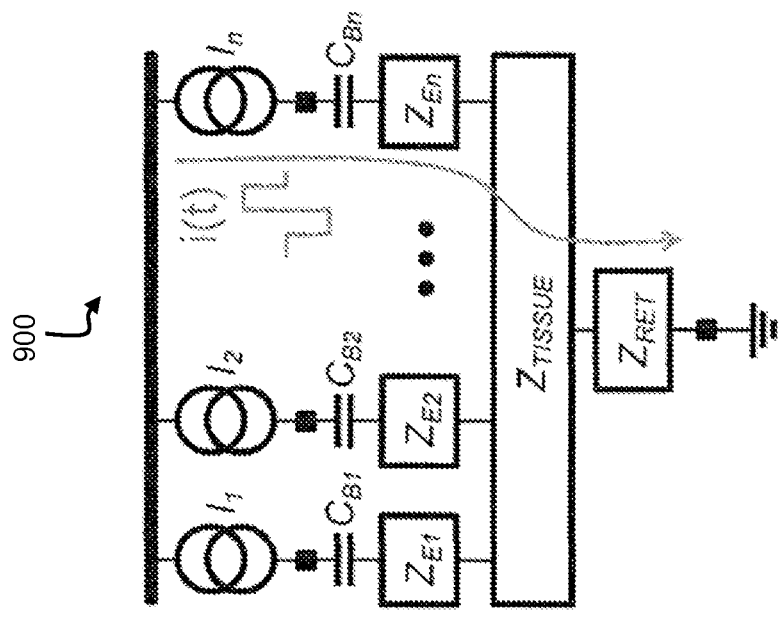

In some implementations, the electronic processor can select a computational model of a nerve fiber (e.g., mammalian myelinated nerver fiber) to calculate the energy of various waveforms. For example, the Hodgkin-Huxley type discrete cable model can be used as the computational model of a single nerve fiber. FIGS. 9A-C are schematics of a computational model 900 used for calculating a trigger of action potential for various stimulus waveforms. Model 900 can include "n" current sources ($I_1$ to $I_n$), electrodes, and target neural tissue (also referred to as a neural fiber). FIG. 9A depicts path stimulation current i(t) from the ith current source $I_i$ (i=1 to n) through an optional DC blocking capacitor $C_{Bi}$ (e.g., 100-900 nF) to the intercochlear electrodes $Z_{Ei}$. FIG. 9B shows a model of the impedance of electrodes $Z_{Ei}$. In this model $C_d$ represents the double-layer capacitance at the electrode-fluid interface at the cochlear, and $R_s$ is the fluid resistance. Values of 5-50 nF and 2-10 kW can be used for $C_d$ and $R_s$, respectively, to calculate power dissipated in each electrode $Z_{Ei}$.

From the intracochlear electrodes $Z_{Ei}$, current spreads through the tissue, cartilage, and bone. Assuming the tissue to be homogeneous and isotropic with a resistivity of $r_e$ (e.g., about 300 W×cm), voltage $V_e$(t) generated in the tissue by stimulation current i(t) at a distance "r" from electrode $Z_{Ei}$ can be calculated according to Eq. (5):

$$V_e(t) = \frac{r_e i(t)}{4pr}. \qquad (5)$$

The calculated $V_e$(t) can be applied to a nerve fiber model (e.g., Hodgkin-Huxley type discrete cable model) as a extracellular potential to determine whether an action potential is triggered. The calculations can be repeated for various waveforms to determine which waveform with less energy can trigger the action potential. FIG. 9A shows i(t) with a biphasic rectangular pulse as an example, however, the electronic processor can carry out the calculation of an arbitrary shape of i(t), and compare the energy for different shapes. From the tissue, current i(t) is collected by a common extracochlear return electrode $Z_{RET}$, which impedance is typically smaller than that of electrodes $Z_{ei}$.

Electronic processor can generate and optimize the waveforms in several approaches. For example, the electronic processor can utilized a heuristic algorithm such as a genetic algorithm (GA) to determine a highly energy efficient waveform shape. Other algorithms such as a simulated annealing algorithm can also be utilized. The electronic processor implementing a genetic algorithm can be configured to:

(a) for a first generation of population, randomly generate multiple waveforms spanning the space of possible solutions;

(b) calculate a fitness quotient (e.g., energy of the waveform) for each waveform of the population;

(c) select waveforms with low energies as parent solutions that are used to generate waveforms in the second generation;

(d) generate a second generation of population, where two parent solutions are selected and their characteristics are blended and mutated together; and (e) repeating steps (b)-(d) for a larger number of generations until one or more waveforms with energies lower than a predetermined threshold is met. Parameters of such one or more waveforms can be sent to digital waveform interface 602.

In some implementations, a genetic algorithm can begin with an initial population of 50 waveforms, each discretized to 20 time steps (also referred as "genes"). Duty of the waveform can be constrained such that the cathodic and anodic phases have same phase widths. For example, each phase can include 10 time steps, which can provide sufficient degrees of freedom to simulate an arbitrary waveform shape. In some implementations, the duty cycle of the cathodic and anodic phase can differ so that each phase has a different number of time steps. For example, the ratio of the pulse width of the cathodic and anodic phases can be 40:60 or less (e.g., 30:70 or less). An example is described in relation to FIG. 3-9 in U.S. Provisional Application 61/908,237 filed on Nov. 25, 2013, the entire contents of which are incorporated herein by reference. As described herein, both cathodic and anodic phase need not be constrained to be rectangular in shape so that efficiency enhancement of both the cathodic and anodic phase is carried out. The fitness quotient can be calculated as the energy of the waveform plus an energy penalty if no action potential is triggered to filter out the unfit waveforms. The genetic algorithm can be carried out for a large number of generations of 5000 or more (e.g., 7500 or more, 10000 or more, 12500 or more, or 15000 or more).

Figure 10A:
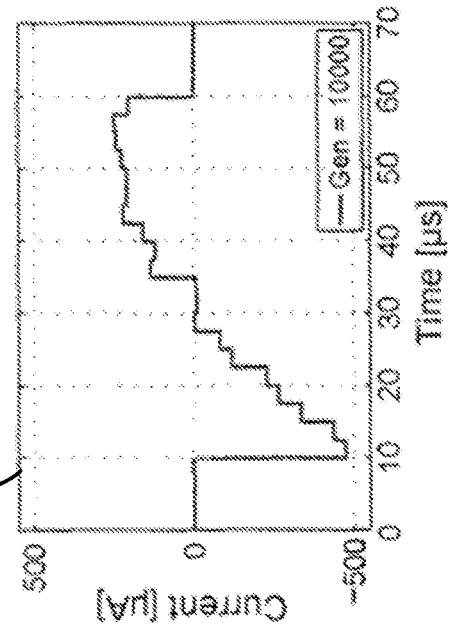
FIGS. 10A-C are plots showing an evolution of an example of a waveform and its energy.
Figure 10B:
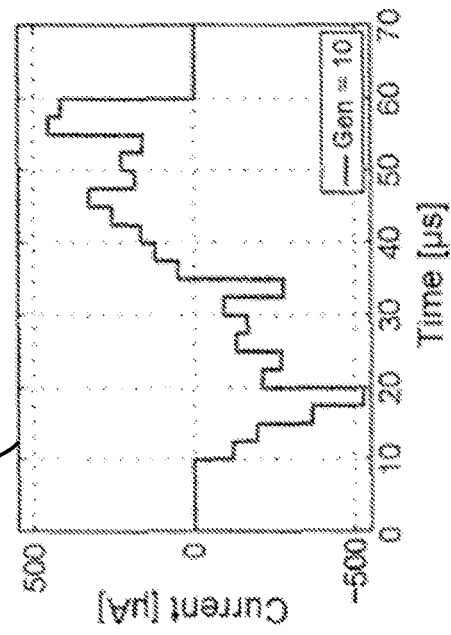
Figure 10C:
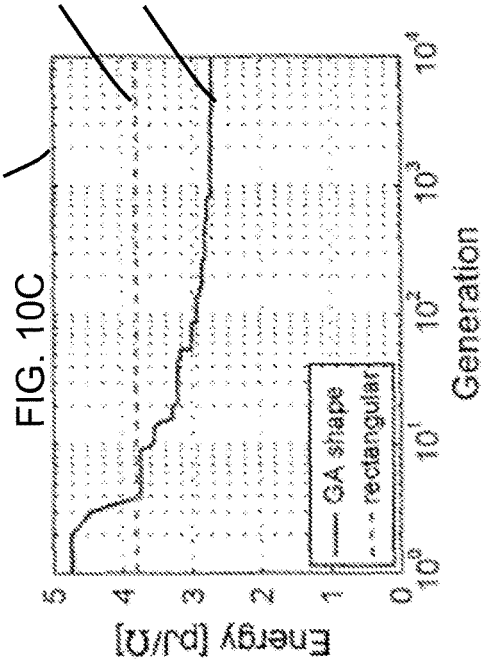

An electronic processor can be configured to produce an evolution of a waveform over generations of 1, 10, 100, 1000, 10000 or more. Total pulse duration of the waveform can be 100 μs or less (e.g., 50 μs or less). When the duty cycle between the cathodic phase and the anodic phase of the waveform is 50:50 with no inter-phase gap, phase width of two phases can each be 50 μs or less, 25 μs or less). FIGS. 10A-C show plots 1010, 1020, and 1030 showing an evolution of an example waveform and its energy for a total pulse duration of 50 μs, where the cathodic phase and anodic phase each 20 μs phase width. For plots 1010 and 1020, x-axes show the time of the waveform and y-axes show current amplitude. The cathodic phase starts from 10 μs to 35 μs, and the anodic phase starts from 35 μs to 60 μs. FIG. 10A shows the waveform after 10 generations, and FIG. 10B shows the waveform after 10000 generations. Solid line 1032 of FIG. 10C shows the energy evolution of the waveform over the number of generations, and dashed line 1034 shows energy of biphasic rectangular waveform having both rectangular cathodic and anodic phases as shown in FIG. 8 with no inter-phase gap. Dashed line 1034 has an energy of about 3.8 pJ/W and solid line 1032 has an energy of about 2.8 pJ/W for triggering an activation potential, respectively.

Accordingly, the evolved waveform (represented by solid line 1032) can be about 28% more energy-efficient after about 10000 generations than the biphasic rectangular waveform (represented by dash line 1034). In some implementations, the evolved waveforms can be 35% or more (e.g., 54% or more) energy-efficient. The cathode phase of the evolved waveform can resemble (but not exactly be) a decreasing exponential cathodic phase, and the anodic phase can resemble a rectangular shape but differs from an exact rectangular shape. In some implementations, the electronic processor can produce waveforms with different total pulse duration and/or different duty cycle between the cathodic phase and the anodic phase.

Figure 11:
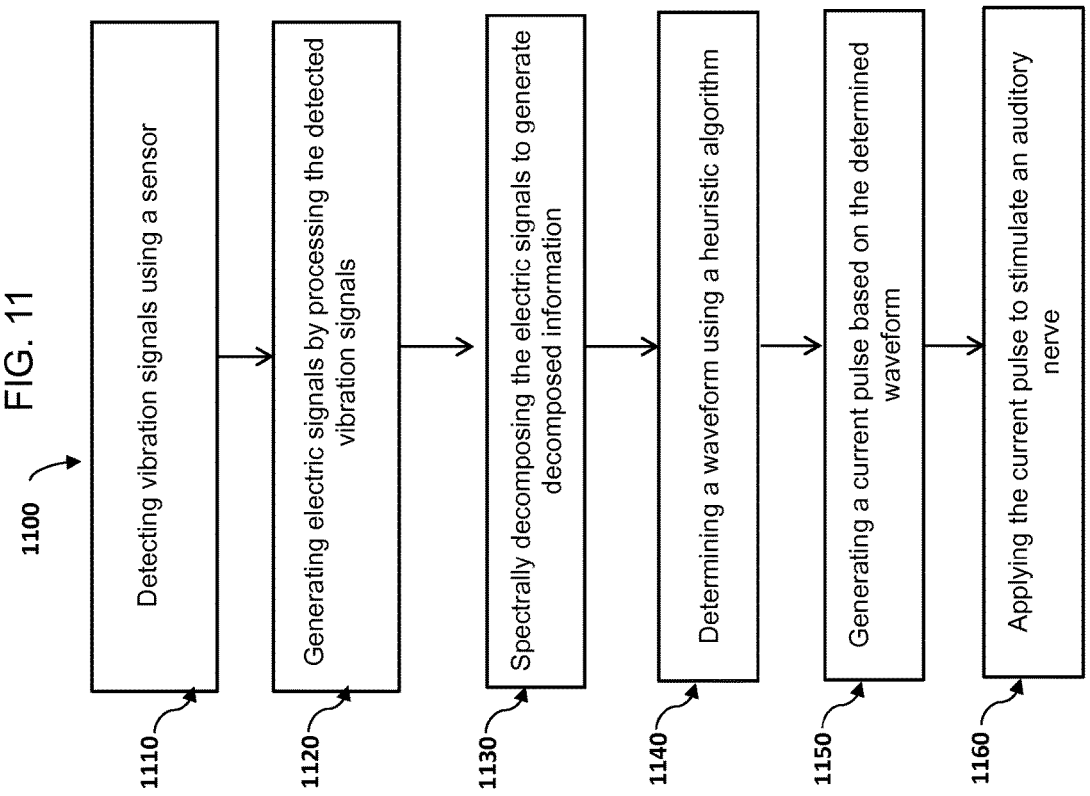
FIG. 11 is a flow chart depicting operations for one example of stimulating auditory nerves of a subject using a cochlear implant as described herein.

Flow chart 1100 in FIG. 11 depicts examples of operations for stimulating auditory nerves of a subject using cochlear implant 200. Operations can include detecting a vibration signal using an acoustic sensor 202 such as a piezoelectric sensor (1110). The vibration can be the vibration of the umbo due to sounds input to an ear of the subject. In some implementations, the acoustic sensor 202 can contact the middle ear within 2 mm or less (e.g., 1 mm or less) of the center of the umbo.

Operations can also include generating electric signals by processing the detected vibration signals using a sensor front-end circuit 204 (1120). In some embodiments, the sensor front-end circuit 204 can be electrically impedance matched to acoustic sensor 202 to efficiently collect current from the acoustic sensor 202. The sensor front-end circuit 204 can amplify the signal and convert the amplified signal into a digital signal using an ADC 305.

Sound processor circuit 206 spectrally decomposes the converted electric signals to generate decomposed information for multiple channels of the sound processor circuit 206 (1130). Different channels represent different frequencies of sound. The spectral decomposition can be achieved by passing through the converted signal to a 3-stage decimation filter 312 and filter bank 314. The decomposed signal is passed onto an extractor 316 for extracting an envelope for each channel. The envelope extracted by extractor 316 can be processed through compressor 318 and fitting circuit 320 as described in relation to sound processor circuit 206 in the preceding paragraphs.

Operations can also include determining a waveform using a heuristic algorithm such as a genetic algorithm, using, for example, an electronic processor (1140). The electronic processor can generate waveforms over an evolution over multiple generations (e.g., 10000). The electronic processor can calculate energy of the waveforms over the multiple generations. The electronic processor can stop the evolution after a fixed number of generations or after the energy reaches a predetermined threshold. In some implementations, the electronic processor can be configured to fix or adjust the total pulse width, duty cycle, number of steps/phase, inter-phase gap, for example, depending on the used computational model. The determined waveform can have both its cathodic phase and anodic phase differ from a rectangular shaped waveform. This operation can be done once and parameters of the determined waveform can be used repeatedly to generate electrical stimulus pulses over an extended period of time by cochlear implant 200. In some cases, the electronic processor can be prompted to recalculate a new waveform to take into account any changes of the subject or environmental conditions.

A current pulse can be generated based on the determined waveform in operation 1140 (1150) by sending parameters of the determined waveform to a waveform stimulator 208, which can generate a current pulse shaped according to the determined waveform. The waveform stimulator 208 can include a digital waveform interface circuit 602, a current source 604, and an electrode switch matrix 606 that are used in combination to generate the current pulse and apply the current pulse to electrode array 210.

Operations can also apply the current pulse to stimulate an auditory nerve by passing through multiple electrodes of the electrode array 210 (1160). The magnitude of the current pulse for each electrode can be controlled by the waveform stimulator 208 based on the decomposed information in operation 1130. Each electrode can correspond to a particular frequency band of sound to be perceived by a subject. When a large magnitude of current pulse is applied to a specific electrode, the subject may perceive a large sound for the frequency band represented by the specific electrode.

In some implementations, determination of the waveform in operation 1140 can be implemented before cochlear implant 200 is implanted into the subject. For example, a high efficiency waveform can be determined and loaded and saved on waveform stimulator 208. This approach can be taken when there is little or no need to change the shape of current pulses generated by the waveform stimulator 208 over an extended period of the use of the cochlear implant 200. In some implementations, operation 1140 can be implemented after the cochlear implant 200 is implanted to the subject. For example, the waveform stimulator 208 can include an electronic processor and memory that executes a code to determine a high efficiency waveform based on the disclosed techniques in this specification. The high efficiency waveform can be fitted to a specific patient by the electronic processor calculating a genetic algorithm and receiving input from the subject on whether the subject perceives sound for various waveforms generated by the algorithm.

Examples of operations depicted in FIG. 11 need not be carried out in the order shown in FIG. 11. In some implementations, some operations shown in FIG. 11 can be omitted. For example, operation 1140 can be omitted when the waveform is predetermined.

In some cases, the high efficiency waveform can be re-accessed over time while the cochlear implant 200 is implanted to reflect any condition changes of the subject. Electronic processor, which may be included in cochlear implant 200 or external to cochlear implant 200 can function as a calibration circuit configured to measure hearing thresholds (e.g., by receiving input from the subject) for various of waveform shapes and select a waveform shape having a low energy of 3.5 pJ/W or less (e.g., 3.2 pJ/W or less, 2.8 pJ/W or less). The electronic processor need not calculate a high efficiency waveform every time the cochlear implant 200 generates a pulse. Therefore, in some implementations, the electronic processor can be external, and for example, send any recalculated waveform parameters wirelessly using WiFi, Bluetooth, or near field communication (NFC) to the cochlear implant 200 when needed.

During use of cochlear implant 200, the number of channels for sound processing can be adjusted. For example, the channel mode can be changed between 4-, 6-, and 8-channel modes. In some implementations, the number of channels can be 12 or more (e.g., 16 or more, 22 or more), and the channels be reconfigured. Such reconfigurability can be used to reduce power consumption depending on a subject's needs and the battery capacity of the cochlear implant 200. For example, some subjects may only need 6 channels to have good sound perception. In this case, the cochlear implant 200 can operate in 6-channel mode instead of 8-channel mode to reduce power consumption. In other examples, cochlear implant 200 can be operating in 8-channel mode when battery 212 is fully charged, but can be changed, either automatically or manually, to operate in 4-channel mode when the battery 212 becomes nearly depleted to save power consumption. For example, the cochlear implant 200 can include a battery level sensor that measures the charge level of the battery 212. When the charge level is below a predetermined threshold (e.g., 20% or less) of the full capacity, the battery level sensor can send a control signal (e.g., via sel_chan) to sound processor circuit 206 to change the channel mode to a lower number of channels to reduce power consumption. In another example, the battery level sensor can send a signal to an external device (e.g., mobile smartphone). The subject can monitor the batter level through the external device, and send a control signal (e.g., via the external device) to sound processor circuit 206 to change the channel mode to a lower number of channels to reduce power consumption.

Performance of Device

Various components of cochlear implant 200 can be manufactured on a single chip using, e.g., a 0.18 μm high-voltage complementary metal-oxide-semiconductor (CMOS) technology. For example, sensor front-end circuit 204, sound processor circuit 206, waveform stimulator 208, electronic processor, and battery 212 of the cochlear implant 200 can be manufactured on a single chip. In some implementations, acoustic sensor 202 can be attached to the middle ear ossicle, such as the incus, stapes, or malleus, e.g., with the umbo of the malleus and electrode array can be attached to the nerve fiber.

The overall power consumption of cochlear implant 200 can be less than 600 μW during operation for normal conversation. For example, the cochlear implant 200 can consume 600 μW or less for detecting an input sound of 70 dB SPL and stimulating a subject with totally impaired cochlear function to perceive the detected sound as 70 dB SPL, which is at about the same level as a subject with normal hearing. This can enable 21 hours of operation from a single 5 g ultra-capacitor with an energy density of 5 W hr/kg with 50% power conversion efficiency.

In one embodiment, sensor front-end circuit 204 can consume 6.83 μA and a power of 10.3 μW or less from a 1.5 V power supply. This is about two orders of magnitude smaller than the case using op-amps consuming 660 μW from a 3.3 V power supply. The sensor front-end circuit 204 can accommodate a range of sensor sizes and masses.

Sound processor circuit 206 can consume 1.6 μW or less from a 0.6 V power supply when operating in the 8-channel mode. In some implementations, the power consumption can be scaled linearly within 15% or less (e.g., 10% or less, 5% or less) according to the number of channels in operation. For example, in 4-channel mode, the power consumed can be 0.8 μW. In some implementations, ADC 305 and sound processor circuit 206 can together consume 1.9, 1.57, or 1.43 μW or less of power from a 0.6 V supply in 8/6/4-channel modes, respectively.

Waveform stimulator 208 can provide energy-efficient stimulation pulses to reduce stimulation power. For example, the stimulation power for triggering the activation potential of a nerve fiber can be reduce by 23% at a phase width of 31.25 μs when compared to a biphasic rectangular waveform. In some implementations, waveform stimulator 208 can consume 560, 413, or 269 µW in the 8-, 6-, and 4-channel modes.

Various examples and methods are disclosed at, for example, portions titled Chapters 3-5 in U.S. Provisional Application 61/908,237 filed on Nov. 25, 2013, the entire contents of which are incorporated herein by reference.

General Applications

The disclosed techniques can be used to implement fully implantable cochlear implants for assisting hearing in subjects with conductive hearing loss or sensorineural hearing loss. As the disclosed cochlear implants can be very small and manufactured on a single chip, the implants can be fully implantable and contained inside the ear so that subjects can use the cochlear implants in the shower and during water sports. The low-power design of the cochlear implants allows the subjects to use the implants over an extended period of time, thereby providing convenience of use.

Other Uses

The disclosed techniques can be applied in applications other than stimulating auditory nerves. For example, the techniques can be applied to other neural prostheses like retinal or vestibular implants, or therapeutic devices such as deep brain stimulators, or other devices that deliver electrical stimulation of a neural tissue. Neural prostheses and implantable therapeutic devices such as deep brain stimulators or vagal nerve stimulators can be used for treatment of Parkinson's disease, essential tremor, and epilepsy. Because such devices rely on delivering electrical current pulses into nerve tissues to elicit neural responses, the techniques disclosed herein can be used to provide devices with low-power consumption and generating energy-efficient stimulus waveforms.

For example, in some implementations, a nerve stimulator device can include various components such as a digital waveform interface circuit 602, a current source 604, and an electrode switch matrix 606 of waveform simulator 208 described herein. The nerve stimulator device can be used in applications described in the preceding paragraph. Moreover, the techniques described in preceding sections for determining an energy-efficient waveform, for example, using a heuristic algorithm, can be used to generate electrical stimulation pulses. In some cases, only one electrode can be used to stimulate a neural tissue without utilizing an electrode select state machine. In some cases, multiple electrodes can be used to apply stimulation pulses to different tissues. The stimulator device can include an electrode select state machine that receives control signals for selecting which electrodes to apply stimulation pulses.

EXAMPLES

The methods and systems described herein are further illustrated using the following examples, which do not limit the scope of the claims.

Example 1—Fully-Implantable Cochlear Implant

Figure 12:
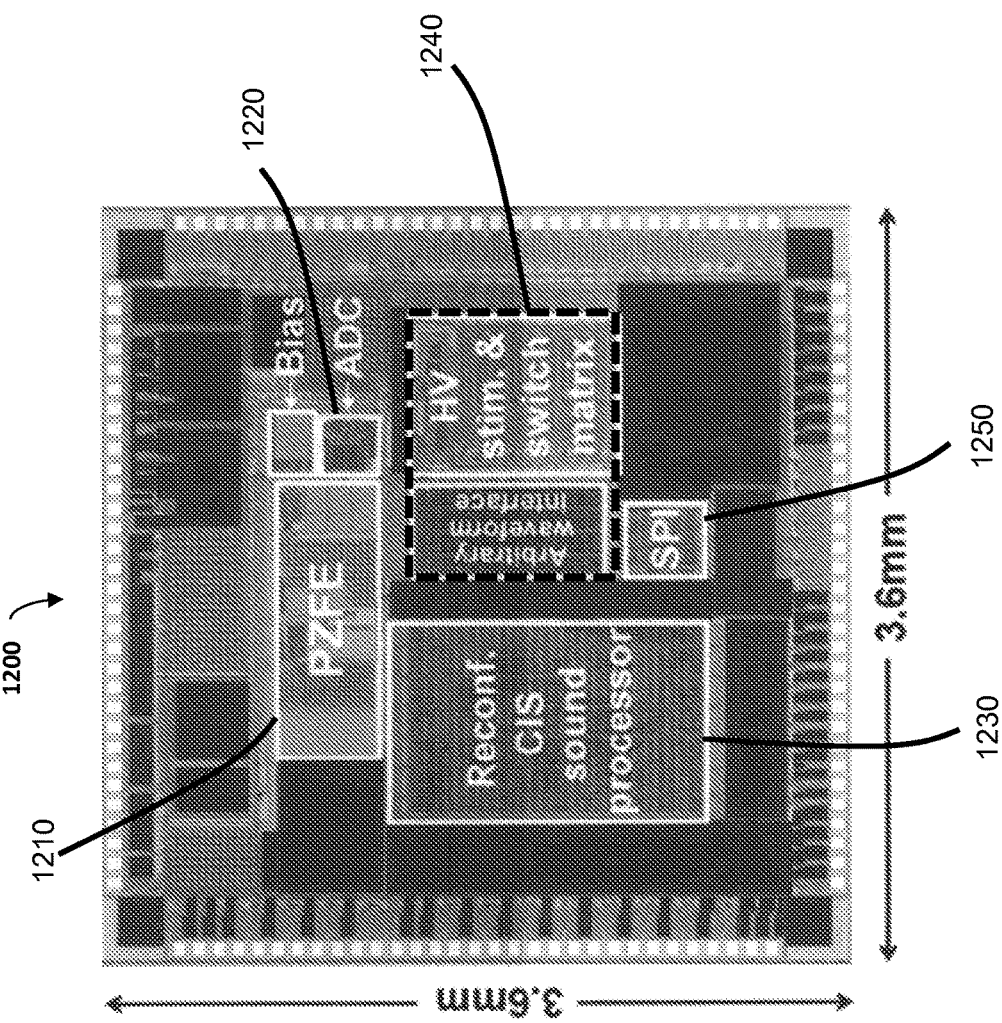
FIG. 12 is a representation of a manufactured fully-implantable cochlear implant chip.

FIG. 12 shows an image 1200 of a manufactured fully-implantable cochlear implant chip. The chip has a size of 3.6 mm×3.6 mm while the active die area is 3.3 mm$^2$ The chip was fabricated by 0.18 µm high-voltage CMOS technology and packaged in a 128-lead think quad flat package (QFP) package. The chip includes a sensor front-end circuit 1210, sound processor circuit 1230, waveform stimulator 1240, and SPI 1250. In this chip, ADC 1220 is located adjacent to sensor front-end circuit 1210. The sensor front-end circuit 1210 operated with a supply voltage of 1.5 V and the sound processor circuit 1230 operated with a supply voltage of 0.6 V. The ADC 1220 operated at a supply voltage of 0.6 V. The chip were reconfigurable to operate in 4-, 6-, 8-channel modes. Example specifications and power consumption of the chip are described in relation to Table 5-4 in U.S. Provisional Application 61/908,237 filed on Nov. 25, 2013, the entire contents of which are incorporated herein by reference.

Example 2—Sound Processor Circuit

The sound processor circuit 1230 shown in FIG. 12 was tested using an arbitrary function generator (AFG3102 from Tektronix) to generate arbitrary test signals at the input of the ADC 1220. Outputs (dstimA[5:0] through dstimH[5:0]) of the sound processor circuit 1230 were recorded and reconstructed using a computer. All measurements with the ADC 1220 and sound processor circuit 1230 were made at a digital supply voltage of 0.6 V.

Figure 13C:
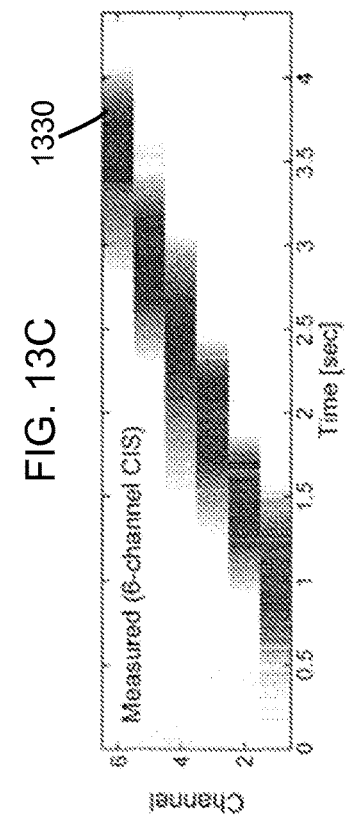
FIGS. 13A-D are images showing a demonstration of the reconfigurability in the number of channels of a sound processor circuit.
Figure 13D:
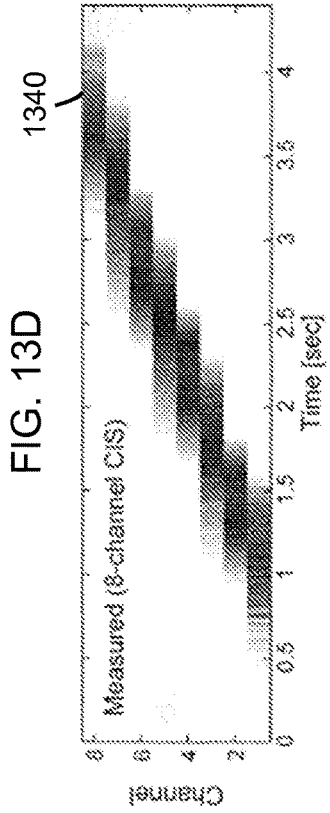
Figure 13A:
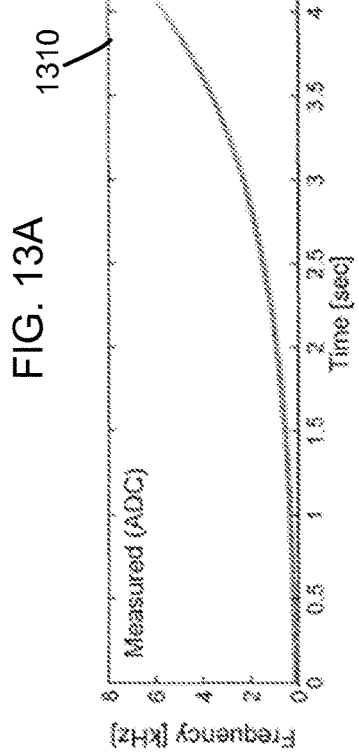
Figure 13B:
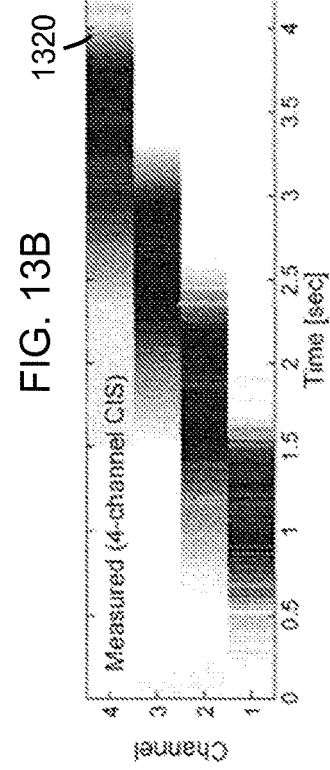

FIGS. 13A-D are images showing a demonstration the ability of the new systems to reconfigure the number of channels of the sound processor circuit 1230. A logarithmic chirp signal was input to the ADC 1220. FIG. 13A is a plot 1310 showing the measured spectrogram at the output of the ADC 1220. FIG. 13B is a plot 1320 showing the measured spectrogram of the sound processor circuit 1230 configured in a 4-channel mode. FIG. 13C is a plot 1330 showing the measured spectrogram of the sound processor circuit 1230 configured in a 6-channel mode. FIG. 13D is a plot 1340 showing the measured spectrogram of the sound processor circuit 1230 configured in an 8-channel mode. Because the sound processor circuit 1230 used a logarithmically spaced filter bank, the measured spectrograms were linear. The measured results show that the sound processor circuit 1230 provides spectrograms resembling the input chirp signal. Simulation results (not shown) show good agreement with the measured results.

The sound processor circuit 1230 had good patient-fitting capabilities for controlling the adjustable threshold (THR) and the most-comfortable-level (MCL), which can be set individually for each channel.

Example 3—Waveform Stimulator

An electronic processor and waveform stimulator were used to generate a variety of waveforms by implementing a genetic algorithm. Several examples are described in this section.

Figure 14A:
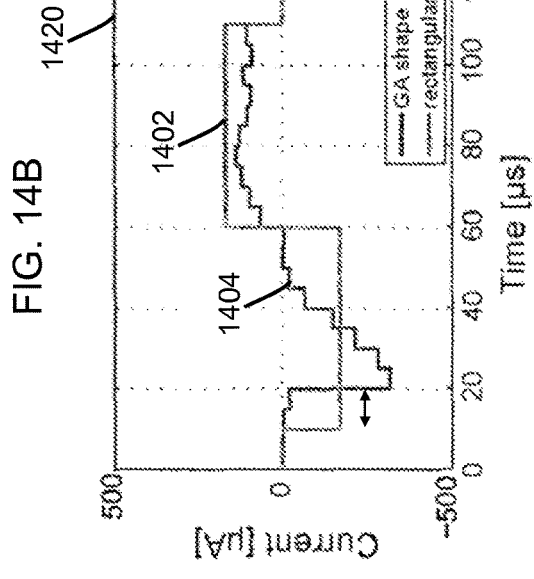
FIGS. 14A-C are plots of energy efficient waveforms for various pulse width.
Figure 14B:
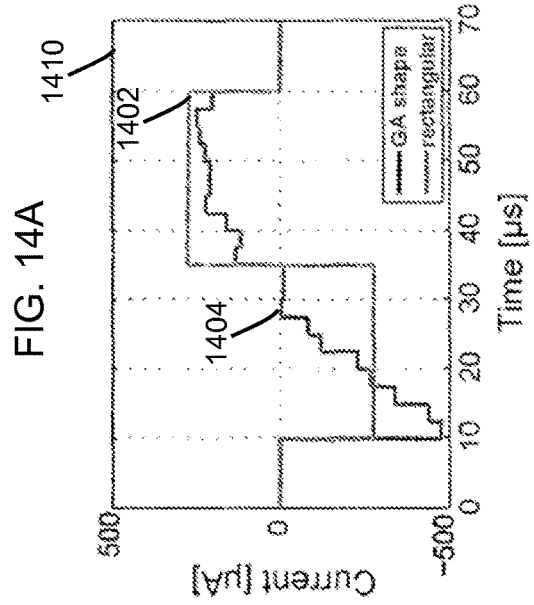
Figure 14C:
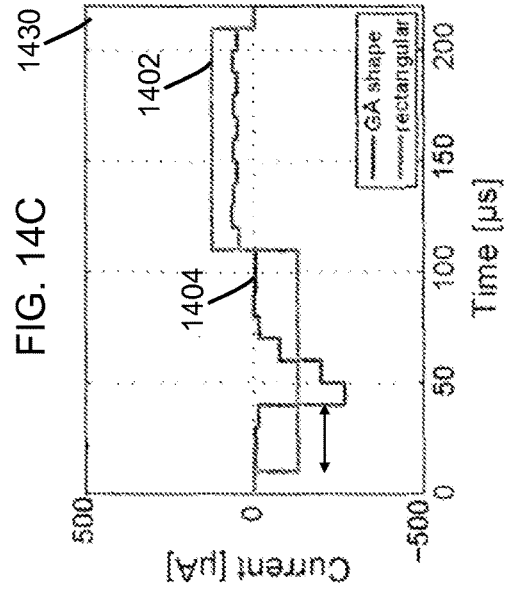

Waveforms were generated over various phase widths. FIGS. 14A-C are plots of energy efficient waveforms for various pulse width. FIG. 14A is a plot 1410 showing the energy efficient waveform for pulse width of 25 µs. FIG. 14B is a plot 1420 showing the energy efficient waveform for pulse width of 50 µs. FIG. 14C is a plot 1430 showing the energy efficient waveform for pulse width of 100 µs. Each waveform in plots 1410-1430 are obtained with 10 steps/phase after 10,000 generations through a genetic algorithm. Phase widths can be generated, but not limited to, from 10 µs to 200 µs. The generated high efficiency waveforms are labeled as 1404 in all three plots. For comparison, a biphasic rectangular waveform at threshold for each of the corresponding phase widths are drawn and labeled as 1402. The waveforms 1404 in plots 1410, 1420, and 1430 have an energy of 2.71 pJ/W, 1.84 pJ/W, and 1.49 pJ/W, respectively, for threshold of triggering activation of nerves. Corresponding energy savings relative to waveform 1402 were 28%, 35%, and 54%, respectively. For plot 1410, the current of the cathodic phase is nonzero over the entire cathodic phase. In contrast, for plots 1420 and 1430, the genetic algorithm determined that it was not beneficial to deliver charge at the start or the end of the cathodic phase, effectively concentrating most of the current over a 30-40 µs window in the middle of the cathodic phase. Accordingly, energy savings may increase for longer pulse widths.

Waveforms with uneven splits of duty cycles were generated. For example, the duration of the cathodic and anodic phases were allowed to be arbitrary and independent from one another. The total durations were fixed. The results showed that the anodic phased started earlier and the resulting duty cycle was 40:60 for the cathodic and anodic phases.

The number of "genes" (time steps/phase) of the genetic algorithm were adjusted. For example, the waveforms were calculated for pulse width of 50 µs with 5, 10, and 20 steps/phase. The results showed that the waveform had a trend of decreasing front-loaded cathodic phase followed by a relatively flat anodic phase. However, the cathodic phase was not an exact exponential curve and the anodic phase was not an exact rectangular shape.

FIGS. 15A-G are representations of various waveforms generated by an electronic processor and their energies. FIG. 15A is a plot 1510 showing a biphasic waveform with a decreasing exponential cathodic phase and an increasing exponential anodic phase. FIG. 15B is a plot 1520 showing a biphasic waveform with a decreasing exponential cathodic phase and a decreasing exponential anodic phase. FIG. 15C is a plot 1530 showing a biphasic waveform with a decreasing exponential cathodic phase and a rectangular anodic phase. FIG. 15D is a plot 1540 showing a biphasic waveform with an increasing exponential cathodic phase and an increasing exponential anodic phase. FIG. 15E is a plot 1550 showing a biphasic waveform with an increasing exponential cathodic phase and a decreasing exponential anodic phase. FIG. 15F is a plot 1560 showing a biphasic waveform with an increasing exponential cathodic phase and a rectangular anodic phase. FIG. 15G is a plot 1570 showing the waveform energy at the spike threshold of activating a nerve fiber determined for pulse widths from 20 µs to 170 µs for each waveform of plots 1510-1560. In particular, curve 1532, which corresponds to the shape of plot 1530, showed the highest energy saving among the shapes shown in plots 1510-1560. Negative energy in the plots corresponded to energy savings.

In other calculations included varying the time constant for exponentially decreasing cathodic phases. As the time constant became smaller the energy savings increased. For example, a time constant of 10% of the pulse width 150 µs of the cathodic phase showed about a 60% energy saving compared to a biphasic rectangular waveform.

Experiments were carried out to measure the power consumption of waveform stimulator 1240 shown in FIG. 12. A two second audio ("her husband brought some flowers") was played. Measurements were collected with the sound processor circuit 1230 in 8-, 6-, and 4-channel modes, and stimulation phase widths of 25 µs, 31.25 µs, and 50 µs for four different waveform shapes:

(a) rect/rect: rectangular cathodic phase/rectangular anodic phase;

(b) dexp/iexp: decreasing exponential cathodic phase/increasing exponential anodic phase;

(c) dexp/rect: decreasing exponential cathodic phase/rectangular anodic phase; and (d) waveform determined by a genetic algorithm.

The magnitudes of the waveforms were scaled to achieve the same neural response based on nerve fiber simulations. Measurement results are shown in FIGS. 16A-C which are a series of plots of measured power consumption for generating pulses of various waveforms. FIG. 16A is a plot 1610 showing the measured power consumption for phase width of 25 µs. FIG. 16B is a plot 1620 showing the measured power consumption for phase width of 31.25 µs. FIG. 16C is a plot 1630 showing the measured power consumption for phase width of 50 µs. Waveforms (a)-(d) are labeled 1601, 1602, 1603, and 1604, respectively. For all waveforms (a)-(d), power consumption increased with larger pulse width and the number of channels because the current source was active for a longer duration. Waveforms (b)-(d) had led to smaller power consumption than waveform (a) for the same pulse width and number of channels. The waveform (d) of the genetic algorithm was the most power efficient compared to waveforms (a)-(c) and provided a power saving of 22% at pulse width of 25 µs and 29% at pulse width of 50 µs.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An implantable system for providing auditory signals to a subject, the system comprising:
   a sensor front-end circuit configured to be connected to an acoustic sensor and to convert analog signals received from the acoustic sensor to digital electric signals; and
   a sound processor circuit configured to be connected to the sensor front-end circuit and receive the electrical signals provided by the sensor front end circuit;
   wherein:
   the sound processor circuit comprises multiple filters that spectrally decompose the received electrical signals into multiple spectral channels during operation of the system;
   the multiple spectral channels comprise at least a low frequency channel and a high frequency channel; and
   the sound processor circuit is configured to operate the low frequency channel at a sample rate lower than a sample rate of the high frequency channel, and
   wherein during operation of the system, the system is configured to send a clock signal and a control signal into a gate, and use the output of the gate to clock-gate filters corresponding to spectral channels that are not used to provide the auditory signals.

2. The system of claim 1, wherein the sensor front-end circuit comprises:
   a charge amplifier circuit;
   a programmable gain circuit; and
   an analog-to-digital converter (ADC) circuit.

3. The system of claim 1, wherein the sound processor circuit comprises a reconfigurable filter bank that include the multiple filters, and the reconfigurable filter bank is configured to change the number of spectral channels used to provide auditory signals.

4. The system of claim 3, wherein the sound processor circuit is reconfigurable to operate in 4-channel, 6-channel, or 8-channel modes.

5. The system of claim 3, wherein power consumption of the sound processor circuit is linear to the number of operating spectral channels within 15% or less.

6. The system of claim 3, wherein the reconfigurable filter bank is configured to adjust a bandwidth and center frequency of at least one of the filters.

7. The system of claim 3, wherein the multiple filters are configured to receive coefficients signals input that are quantized to 8-bit precision.

8. The system of claim 1, further comprising a waveform stimulator that comprises:
 a digital waveform interface circuit;
 an electrode switch matrix; and
 a current source.

9. The system of claim 8, wherein the waveform stimulator is configured to provide at least one of: (i) a waveform having a shape that is more energy-efficient than a rectangular waveform with the same pulse width, (ii) a waveform with an adjustable shape, and (iii) a plurality of waveform shapes, wherein the system further comprises a calibration circuit configured to measure hearing thresholds for the plurality of waveform shapes and select a waveform shape having energy that satisfies a threshold condition.

10. The system of claim 8, wherein during operation, the system consumes 600 µW or less during normal conversation.

11. An implantable system for providing auditory signals to a subject, the system comprising:
 a sound processor circuit comprising multiple filters that spectrally decompose received electrical signals into multiple spectral channels during operation of the system; and
 a waveform stimulator comprising a digital waveform interface circuit and an electrode switch matrix, wherein the waveform stimulator is configured to receive output signals from the multiple spectral channels and to generate an auditory signal,
 wherein during operation of the system, the system is configured to send a clock signal and a control signal into a gate, and use the output of the gate to clock-gate filters corresponding to spectral channels that are not used to provide the auditory signals.

12. The system of claim 11, wherein the waveform stimulator comprises a two-stage level shifter that connects the digital waveform interface circuit and the electrode switch matrix.

13. The system of claim 11, wherein the waveform stimulator comprises a single current source.

14. The system of claim 11, wherein the waveform stimulator comprises a fast-settling current source.

15. The system of claim 11, wherein the waveform stimulator is configured to generate a waveform shape which has an energy of 28% or less than that of a rectangular waveform with the same total pulse width.

* * * * *